US008946473B2

(12) United States Patent  
Anderson et al.

(10) Patent No.: US 8,946,473 B2
(45) Date of Patent: Feb. 3, 2015

(54) METHODS OF MAKING L-ORNITHINE PHENYL ACETATE

(75) Inventors: Keith H. Anderson, San Diego, CA (US); Jim Behling, Eagle River, WI (US); Christine Henderson Dougan, Glasgow (GB); Stephen William Watt, Tranent (GB); Peter Manini, Giubiasco (CH); Attilia Figini, Mendrisio (CH)

(73) Assignee: Ocera Therapeutics, Inc., Palo Alto, CA (US)

( * ) Notice: Subject to any disclaimer, the term of this patent is extended or adjusted under 35 U.S.C. 154(b) by 105 days.

(21) Appl. No.: 13/878,146

(22) PCT Filed: Oct. 5, 2011

(86) PCT No.: PCT/US2011/054983
§ 371 (c)(1),
(2), (4) Date: Apr. 5, 2013

(87) PCT Pub. No.: WO2012/048043
PCT Pub. Date: Apr. 12, 2012

(65) Prior Publication Data
US 2013/0211135 A1 Aug. 15, 2013

Related U.S. Application Data

(60) Provisional application No. 61/390,585, filed on Oct. 6, 2010.

(51) Int. Cl.
*C07C 227/18* (2006.01)
*C07C 229/26* (2006.01)
*A61K 31/192* (2006.01)
*A61K 31/198* (2006.01)
*C07C 51/41* (2006.01)

(52) U.S. Cl.
CPC .......... *C07C 227/18* (2013.01); *A61K 31/192* (2013.01); *A61K 31/198* (2013.01); *C07C 51/412* (2013.01)
USPC ....................................................... 562/496

(58) Field of Classification Search
CPC .. A61K 31/198; A61K 31/192; C07C 227/18; C07C 229/26; C07C 57/46
USPC ....................................................... 562/496
See application file for complete search history.

(56) References Cited

U.S. PATENT DOCUMENTS

| 3,950,529 | A | 4/1976 | Fischer et al. |
| 4,100,293 | A | 7/1978 | Walser |
| 4,228,099 | A | 10/1980 | Walser |
| 4,284,647 | A | 8/1981 | Brusilow et al. |
| 4,320,146 | A | 3/1982 | Walser |
| 4,352,814 | A | 10/1982 | Walser |
| 4,457,942 | A | 7/1984 | Brusilow et al. |
| 5,405,761 | A | 4/1995 | Makryaleas et al. |
| 5,571,783 | A | 11/1996 | Montagne et al. |
| 5,591,613 | A | 1/1997 | Makryaleas et al. |
| 6,083,953 | A | 7/2000 | Nestor et al. |
| 6,258,849 | B1 | 7/2001 | Burzynsk |
| 6,451,340 | B1 | 9/2002 | Arimilli et al. |
| 6,503,530 | B1 | 1/2003 | Kang et al. |
| 6,514,953 | B1 | 2/2003 | Armitage et al. |
| 6,768,024 | B1 | 7/2004 | Watson-Straughan et al. |
| 6,943,192 | B2 | 9/2005 | Burzynski |
| 8,173,706 | B2 | 5/2012 | Anderson et al. |
| 8,389,576 | B2 | 3/2013 | Jalan et al. |
| 8,492,439 | B2 | 7/2013 | Anderson et al. |
| 2003/0195255 | A1 | 10/2003 | Summar |
| 2004/0152784 | A1 | 8/2004 | March |
| 2004/0229948 | A1 | 11/2004 | Summar et al. |
| 2005/0182064 | A1 | 8/2005 | Burzynski |
| 2006/0045912 | A1 | 3/2006 | Truog |
| 2008/0119554 | A1 | 5/2008 | Jalan et al. |
| 2012/0157526 | A1 | 6/2012 | Jalan et al. |
| 2012/0208885 | A1 | 8/2012 | Anderson et al. |
| 2012/0259016 | A1 | 10/2012 | Jalan et al. |
| 2013/0211135 | A1 | 8/2013 | Anderson et al. |
| 2013/0296429 | A1 | 11/2013 | Anderson et al. |

FOREIGN PATENT DOCUMENTS

| CN | 1383815 | 12/2002 |
| CN | 102421432 A | 4/2012 |
| EP | 1179347 | 2/2002 |
| EP | 1334722 | 8/2003 |
| EP | 1374863 | 1/2004 |
| EP | 1541141 | 6/2005 |
| GB | 965637 | 8/1964 |
| GB | 1067742 | 5/1967 |

(Continued)

OTHER PUBLICATIONS

Bruha et al., "Effect of carvedilol on portal hypertension depends on the degree of endothelial activation and inflammatory changes", Scand J Gastroenter. (2006) 41: 1454-1463.
Jiang et al., "L-Ornithine-l-aspartate in the management of hepatic encephalopathy: a meta-analysis", J Gastroenterol Hepatol. (2009) 24(1): 9-14; Available online: Sep. 24, 2008.
Lopez-Talavera et al., "Thalidomide Inhibits Tumor Necrosis Factor alpha, Decreases Nitric Oxide Synthesis, and Ameliorates the Hyperdynamic Circulatory Syndrome in Portal-Hypertensive Rats", Hepatology (1996) 23(6): 1616-1621.
Maev I.V. Primenenie preparata L-ornitin-L-aspartata v kompleksnoy terapii pechyonochnoy entsefalopatii u bolnykh tsirrozom pecheni. Rossiyskiy zhurnal gastroenterologii, gepatologii, koloproktologii, 2002, No. 6, pp. 60-66.

(Continued)

*Primary Examiner* — Yevegeny Valenrod
(74) *Attorney, Agent, or Firm* — Knobbe Martens Olson & Bear LLP

(57) ABSTRACT

Disclosed herein are processes for making L-ornithine phenyl acetate. The process may include, for example, inter-mixing a halide salt of L-ornithine with silver phenyl acetate. The process may also include forming a phenyl acetate salt in situ. The present application also relates to various compositions obtained from these processes, including crystalline forms.

34 Claims, 22 Drawing Sheets

(56) References Cited

FOREIGN PATENT DOCUMENTS

| GB | 1080599 | 8/1967 |
|---|---|---|
| GB | 1310658 | 3/1973 |
| GB | 1507951 | 4/1978 |
| JP | 54-163518 A | 12/1979 |
| JP | 05221858 | 8/1993 |
| MX | 2003009902 A | 5/2005 |
| WO | WO 85/04805 | 11/1985 |
| WO | WO 97/30167 | 8/1997 |
| WO | WO 00/71151 | 11/2000 |
| WO | WO 02/34255 | 5/2002 |
| WO | WO 02/074302 | 9/2002 |
| WO | WO 03/037378 | 5/2003 |
| WO | WO 03/045372 | 6/2003 |
| WO | WO 03/086074 | 10/2003 |
| WO | WO 2004/019928 | 3/2004 |
| WO | WO 2005/053607 | 6/2005 |
| WO | WO 2006/056794 | 6/2006 |
| WO | WO 2006/059237 | 6/2006 |
| WO | WO 2010/115055 | 10/2010 |

OTHER PUBLICATIONS

Trebicka et al., Atorvastatin lowers portal pressure in cirrhotic rats by inhibition of RhoA/Roh-kinase and activation of endothelial nitric oxide synthase, Hapatology, (2007) 46(1): 242-253.
Wright et al., "Reduction in Ammonia with L-Ornithine, Phenylacetate (OP) but not Anti-TNF Prevents LPS Induced Brain Edema in Bile-duct Ligated Cirrhotic Rats", Abstract 773; J Hepatology (2009) 50: S283.
International Search Report and Written Opinion dated Dec. 9, 2011 for Application No. PCT/US2011/054983, filed Oct. 5, 2011.
International Preliminary Report on Patentability dated Apr. 9, 2013 for Application No. PCT/US2011/054983, filed Oct. 5, 2011.
Berg et al., "Pharmacokinetics and cerebrospinal fluid penetration of phenylacetate and phenylbutyrate in the non-human primate", Cancer Chemother. Pharmacol. (May 2001) 47(5): 385-390. Abstract Only.
"Sodium phenylbutyrate for urea cycle enzyme deficiencies." [No authors listed], Med Lett Drugs Ther., Nov. 22, 1996, vol. 38, Issue 988, pp. 105-106.
Aggarwal et al., "Predictors of Mortality and Resource Utilization in Cirrhotic Patients Admitted tothe Medical ICU", Chest, 2001, vol. 119, Issue 5, pp. 1489-1497.
Al-Hassnan et al., "The relationship of plasma glutamine to ammonium and of glycine to acid-base balance in propionic acidaemia", J. Inherit. Metab. Dis., 2003, vol. 26, pp. 89-91.
Albrecht et al., "Contrasting effects of thioacetamide-induced liver damage on the brain uptake indices of ornithine, arginine and lysine: modulation by treatment with ornithine aspartate", Metab Brain Dis., 1996, vol. 11, Issue 3, pp. 229-237.
Albrecht et al., "Increase of the brain uptake index for L-ornithine in rats with hepatic encephalopathy", Neuroreport, 1994, vol. 5, Issue 6, pp. 671-673.
Als-Nielsen, Bodil, et al., Non-Absorbable Disaccharides for Hepatic Encephyalopathy: Systematic Review of Randomised Trials, BMJ, 2004, p. 1-6.
Anadiotis et al., "Ornithine transcarbamylase deficiency and pancreatitis", J Pediatr, 2001, vol. 138, pp. 123-124.
Bachmann et al., "Ammonia toxicity to the brain and creatine", Molecular Genetics and Metabolism, 2004, vol. 81, pp. S52-S57.
Balata et al., "Induced hyperammonemia alters neuropsychology, brain MR spectroscopy and magnetization transfer in cirrhosis,", Hepatology, 2003, vol. 4, Issue 37, pp. 931-939.
Batshaw et al., "Alternative pathway therapy for urea cycle disorders: twenty years later", J Pediatr, 2001, vol. 138, Issue 1, pp. S46-S55.
Batshaw et al., "Effect of sodium benzoate and sodium phenylacetate on brain serotonin turnover in the Ornithine transcarbamylase-deficient sparse-fur mouse", Pediatric Research, 1988, vol. 23, Issue 4, pp. 368-374.
Beale et al., "Early enteral supplementation with key pharmaconutrients improves sequential organ failure assessment score in critically ill patients with sepsis: outcome of a randomized, controlled, double blind trial,", Crit Care Med., 2008, vol. 1, Issue 36, pp. 131-144.
Berge et al., "Pharmaceutical Salts", J Pharm Sci, 1977, vol. 66(1), pp. 1-19.
Berry et al., "Long-term management of patients with urea cycle disorders", J Pediatri, 2001, vol. 138, Issue 1, pp. S56-S61.
Bighley, L.D., et al.. "Salt Forms of Drugs and Absorption" in Encyclopedia of Pharmaceutical Technology, Eds. J. Swarbrick and J.C. Boylan, vol. 13, Marcel Dekker, Inc., New York, (1996), pp. 453-499.
Blei, Andres T., et al., Pathophysiology of Cerebral Edema in Fulminant Hepatic Failure, Journal of Hepatology, 1999, p. 771-776, vol. 31, Denmark.
Bleichner, et al., "Frequency of infections in cirrhotic patients presenting with acute gastrointestinal haemorrhage", British Journal of Surgery, 1986, vol. 73, Issue 9, pp. 724-726.
Bongers et al., "Exogenous glutamine: the clinical evidence,", Crit Care Med., 2007, vol. 9 Suppl, Issue 35, pp. S545-S552.
Briggs et al., "Effect of Ornithine and Lactate on Urea Synthesis in Isolated Hepatocytes", Biochem J, 1976, vol. 160, pp. 205-209.
Brunquell et al., "Electroencephalographic findings in ornithine transcarbamylase deficiency", J Child Neurol, 1999, vol. 14, Issue 8, pp. 533-536.
Brusilow et al., "Amino acid acylation: A mechanism of nitrogen excretion in inborn errors of urea synthesis", Science, 1980, vol. 207, pp. 659-661.
Brusilow et al., "Treatment of episodic hyperammonemia in children with inborn errors of urea synthesis", The New England Journal of Medicine, 1984, vol. 310, Issue 25, pp. 1630-1634.
Burlina et al., "Long-term treatment with sodium phenylbutyrate in ornithine transcarbamylase-deficient patients", Molecular Genetics and Metabolism, 2001, vol. 72, pp. 351-355.
Butterworth, "Pathophysiology of hepatic encephalopathy: a new look at ammonia", Metab Brain Dis., 2002, vol. 17, Issue 4, pp. 221-227.
Callado França, et al., Five Days of Ceftriaxone to Treat Spontaneous Bacterial Peritonitis in Cirrhotic Patients, Journal of Gastroenterology, Feb. 2002, p. 119-122 vol. 37, No. 2. 119-122 [Abstract Only].
Cavarec et al., "Molecular cloning and characterization of a transcription factor for the copia retrotransposon with homology to the BTB-Containing Lola Neurogenic Factor", Mol. Cell. Biol., 1997, vol. 17, Issue 1, pp. 482-494.
Chainuvati et al., "Ornicetil on encephalopathy. Effect of ornicetil (ornithine alpha-ketoglutarate) on encephalopathy in patients with acute and chronic liver disease", Acta Hepatogastro., 1977, vol. 24, Issue 6, pp. 434-439.
Chen et al., "Continuous arteriovenous hemodiafiltration in the acute treatment of hyperammonaemia due to ornithine transcarbamylase deficiency", Renal Failure, 2000, vol. 22, Issue 6, pp. 823-836.
Clemmesen, et al., Cerebral Herniation in Patients With Acute Liver Failure is Correlated with Arterial Ammonia Concentration, Hepatology, Mar. 1999, p. 648-653, Vo. 29, No. 3, American Association for the Study of Liver Diseases.
Damink et al., Stimulated Liver and Muscle Protein Synthesis by Intravenous Isoleucine Supplementation During a Simulated Variceal Bleed in Patients with Cirrhosis of the Liver, Hepatology, Oct. 2001, AASLD Abstracts #50.
Darmaun et al., "Phenylbutyrate-induced glutamine depletion in humans; effect on leucine metabolism", Am J Physiol Endocrinol Metab., 1998, vol. 274, pp. E801-E807.
Database WPI, Section Ch, Week 200331, Derwent Publications Ltd., London, GB; XP002364873 & CN 1383815 A (Liu W), Dec. 11, 2002 (Abstract Only).
Dejong et al., "Altered glutamine metabolism in rat portal drained viscera and hindquarter during hyperammonemia", Gastroenterology, 1992, vol. 103, Issue 3, pp. 936-948.
Del Rosario et al. , Hyperammonemic encephalopathy, J Clin Gastroenterol, 1997, vol. 25, Issue 4, pp. 682-684.
Demand with Article 34 amendments, filed Feb. 3, 2011, in International Application No. PCT/US2010/029708.
Demand with Article 34 amendments, filed May 16, 2011, in International Application No. PCT/US2010/029708.

(56) References Cited

OTHER PUBLICATIONS

Desjardins et al., "Effect of portacaval anastomosis on glutamine synthetase protein and gene expression in brain, liver and skeletal muscle", Metab Brain Dis., 1999, vol. 14, Issue 4, pp. 273-280.
Dunitz, et al., "Disappearing Polymorphs," *Acc. Chem. Res.* 28:193-200, 1995.
Enns et al., "Survival after treatment with phenylacetate and benzoate for urea-cycle disorders,", N Engl J Med., 2007, vol. 22, Issue 356, pp. 2282-2292.
EPO Examination Report dated Nov. 5, 2008 from EP patent application No. 05808837.8.
EPO Extended European Search Report for EP 09013613.6, dated Jan. 15, 2010.
Fabbri, Andrea et al., Unresponsiveness of Hepatic Nitrogen Metabolism to Glucagon Infusion in Patients with Cirrhosis: Dependence on Liver Cell Failure, Hepatology, 1993, vol. 18, No. 1, pp. 28-35.
Garcia-Tsao, MD, et al., Management and Treatment of Patients with Cirrhosis and Portal Hypertension: Recommendations from the Department of Veterans Affairs Hepatitis C Resource Center Program and the National Hepatitis C Program, Am J Gastroenterol, 2009, p. 1802-1829, Vo. 104.
Garden et al., "Prediction of outcome following acute variceal haemorrhage", Br J Surg., 1985, vol. 72, pp. 91-95.
Gebhardt et al., "Treatment of cirrhotic rats with L-Ornithine-L-Aspartate enhances urea synthesis and lowers serum ammonia levels", J Pharm Exp Thera., 1997, vol. 283, Issue 1, pp. 1-6.
Gonzalez-Navajas et al., "Bacterial DNA in patients with cirrhosis and sterile ascites. Its role as a marker of bacterial translocation and prognostic tool,", Rev Esp Enferm Dig., 2007, vol. 10, Issue 99, pp. 599-603.
Gordon, "Ornithine transcarbamylase deficiency: a urea cycle defect", European Journal of Paediatric Neurology, 2003, vol. 7, pp. 115-121.
Grace et al., "Prevention of initial variceal hemorrhage", Gastroenter Clin North Am., 1992, vol. 21, Issue 1, pp. 149-161.
Greensteine et al., Arch Biochem Biophys, 1956, vol. 64, pp. 342-354.
Grossi et al., "Amino acids mixtures in prevention of acute ammonia intoxication in dogs", Arch Surg, 1967, vol. 94, pp. 261-266.
Häberle et al., Hyperammonämie: Ursachen, Diagnostik, Therapie, Dtsch Med Wochenschr, 2004, pp. 1430-1433, vol. 129 (in German).
Hamberg, Ole et al., Effects of an Increase in Protein Intake on Hepatic Efficacy for Urca Synthesis in Healthy Subjects and in Patients with Cirrhosis, Journal of Hepatology, 1992, pp. 237-243, Elsevier Science Publishers B.V.
Hass et al., "Detection of subclinical and overt hepatic encephalopathy and treatment control after L-Ornithine-L-Aspartate medication by magnetic resonance spectroscopy (1H-MRS)", Z Gastroenterol, 2005, vol. 43, pp. 373-378.
Häussinger et al., "Hepatic encephalopathy in chronic liver disease: a clinical manifestation of astrocyte swelling and low-grade cerebral edema?", J Hepatol., 2000, vol. 32, Issue 6, pp. 1035-1038.
Herlong et al., "The use of ornithine salts of branched-chain ketoacids in portal-systemic encephalopathy", Ann Intern Med., 1980, vol. 93, Issue 4, pp. 545-550.
Honda et al., "Successful treatment of severe hyperammonemia using sodium phenylacetate powder prepared in hospital pharmacy", Biol. Pharm. Bull., [no date], vol. 25, Issue 9, pp. 1244-1246.
Hursthouse, et al., "Why Do Organic Compounds Crystallise Well or Badly or Ever so Slowly? Why . . . ," *Organic Process Research & Development*, 13:1231-1240, 2009.
Igarashi et al., "Determination of ornithine conjugates of some carboxylic acids in birds by high-performance liquid chromatography", Chem Pharm Bull, 1992, vol. 40, Issue 8, pp. 2196-2198.
Inoue et al., "Biochemical analysis of decreased ornithine transport activity in the liver mitochondria from patients with hyperornithinemia, hyperammonemia and homocitrullinuria", Biochim Biophys Acta., 1988, vol. 964, Issue 1, pp. 90-95.

Intellectual Property Office of Singapore (IPOS) Search Report and Written Opinion, dated Apr. 23, 2010, Singapore Patent Application No. 200907712-4.
IPONZ Examination Report dated Apr. 8, 2008 from NZ patent application No. 555870.
International Preliminary Report on Patentability and Written Opinion in International Application No. PCT/US2011/054983, filed Oct. 5, 2011, dated Apr. 18, 2013.
International Preliminary Report on Patentability in International Application No. PCT/GB2005/004539, filed Nov. 28, 2005, dated May 30, 2007.
International Search Report and Written Opinion in International Application No. PCT/US2011/054983, filed Oct. 5, 2011, dated Dec. 9, 2011.
International Search Report and Written Opinion in International Application No. PCT/US2010/029708, filed Apr. 1, 2010, dated Jun. 3, 2010.
International Search Report in International Application No. PCT/GB2005/004539, filed Nov. 28, 2005, issued Feb. 8, 2006.
Iyer et al., "Mouse model for human arginase deficiency", Mol Cell Biol., 2002, vol. 22, Issue 13, pp. 4491-4498.
Jalan et al., "Acute-on-chronic liver failure: pathophysiological basis of therapeutic options", Blood Purif, 2002, vol. 20, pp. 252-261.
Jalan, et al., "L-Ornithine Phenylacetate (OP): A Novel Treatment for Hyperammonemia and Hepatic Encephalopathy", Medical Hypotheses, 2007, p. 1064-1069, vol. 69.
Jalan et al., "Moderate hypothermia in patients with acute liver failure and uncontrolled intracranial hypertension,", Gastroenterology, 2004, vol. 5, Issue 127, pp. 1338-1346.
Jalan et al., "The molecular pathogenesis of hepatic encephalopathy", The International Journal of Biochemistry & Cell Biology, 2003, vol. 35, pp. 1175-1181.
Jalan, M.D., Rajiv, Intracranial Hypertension in Acute Liver Failure: Pathophysiological Basis of Rational Management, Seminars in Liver Disease, 2003, p. 271-282, vol. 23, No. 3, Thieme Medical Publishers, Inc., New York, NY, USA.
Jalan, R., et al., "Treatment of Hyperammonemia in Liver Failure: A Tale of Two Enzymes", Gastroenterology, 2009, p. 2048-2051, vol. 1236.
James et al., "The conjugation of phenylacetic acid in man, subhuman primates and some non-primate species", Proc R Soc Lond B., 1972, vol. 182, pp. 25-35.
Jeyamani et al., Hepatitis E virus and acute-on-chronic liver failure, Indian J Gastroentero., 2004, vol. 23, Issue 2, pp. 45-46.
Kaiser, S. et al., Ammonia and Glutamine Metabolism in Human Liver Slices: New Aspects on the Pathogenesis of Hyperammonaemia in Chronic Liver Disease, European journal of Clinical Investigation , 1988, vol. 18, pp. 535-542.
Kasumov et al., "New secondary metabolites of phenylbutyrate in humans and rats", Drug Metab Dispos., 2004, vol. 32, Issue 1, pp. 10-19.
Katayama, "Ammonia metabolism and hepatic encephalopathy", Hep. Research, 2004, vol. 30, Issue 1, pp. S71-S78.
Khan, et al., Frequency of Spontaneous Bacterial Peritonitis in Cirrhotic Patients with Ascites Due to Hepatitis C Virus and Efficacy of Cirpofloxacin in its Treatment, Gomal Journal of Medical Sciences, Jul.-Dec. 2009, p. 149-154, vol. 7, No. 2.
Kircheis et al., "Therapeutic efficacy of L-ornithine-L-aspartate infusions in patients with cirrhosis and hepatic encephalopathy: results of a placebo-controlled, double blind study,", Hepatology, 1997, vol. 6, Issue 25, pp. 1351-1360.
Lee et al., Acute Liver Failure: Summary of a Workshop, Hepatology, Apr. 2008, p. 1401-1415, vol. 47, No. 4.
Lee, W. M., Acetaminophen-Related Acute Liver Failure in the United States, Hepatology Research, 2008, p. S3-S8, vol. 38, Suppl. 1, The Japan Society of Hepatology.
Linderoth et al., "Short-term prognosis of community-acquired bacteremia in patients with liver cirrhosis or alcoholism: A population-based cohort study,", Alcohol Clin Exp Res., 2006, Issue 30, pp. 636-641.
Lukkarinen, M. et al., Oral Supplementation Corrects Plasma Lysine Concentrations in Lysinuric Protein Intolerance, Metabolism, Jul. 2003, p. 935-938, vol. 52, No. 7.

(56) References Cited

OTHER PUBLICATIONS

MacArthur et al., "Pharmacokinetics of sodium phenylacetate and sodium benzoate following intravenous administration as both a bolus and continuous infusion to healthy adult volunteers", Molecular Genetics and Metabolism, 2004, vol. 81, pp. S67-S73.

Maestri et al., "Long-term treatment of girls with ornithine transcarbamylase deficiency", N Engl J Med., 1996, vol. 335, Issue 12, pp. 855-859.

Maestri et al., "Prospective treatment of urea cycle disorders", J Pediatr., 1991, vol. 119, Issue 6, pp. 923-928.

Maier, K. P. et al., Originalien Activities of Urea-Cycle Enzymes in Chronic Liver Disease, Klinische-Wochenschrift, 1979, vol. 57, pp. 661-665.

Maier, K.P., "herapie der hepatischen Enzephalopathie", Deutsche Med. Wochenzts. 1988, vol. 113, Issue 48, pp. 1886-1889.

Meijer, Alfred J. et al., Nitrogen Metabolism and Ornithine Cycle Function, Physiological Reviews, Jul. 1990, vol. 70, No. 3, pp. 701-748.

Mendenhall et al., "A new therapy for portal systemic encephalopathy", The American Journal of Gastroenterology, 1986, vol. 81, Issue 7, pp. 540-543.

Mihm et al., "Effect of L-ornithine-L-aspartate (LOLA) on neurometabolites in hepatic encephalopathy (HE)", Hepatology, 2001, vol. 34, Issue 4, p. 543A [Abstract Only].

Mizock, MD, FACP, Nutritional Support in Hepatic Encephalopathy, Nutrition, 1999, pp. 220-228, vol. 15, No. 3.

Mizock et al., "Septic Encephalopathy—Evidence for altered phenylalanine metabolism and comparison with hepatic encephalopathy", Arch Intern Med, 1990, vol. 150, pp. 443-449.

Mizutani et al., "Hyperargininemia: Clinical course and treatment with sodium benzoate and phenylacetic acid", Brain Dev., 1983, vol. 5, Issue 6, pp. 555-563.

Moinard et al., "Effects of Ornithine 2-Oxoglutarateon Neutrophils in Stressed Rates: Evidence for the Involvement of Nitric Oxide and Polyamines", Clin Sci, 2002, vol. 102, Issue 3, pp. 287-295.

Mookerjee et al., "Neutrophil dysfunction in alcoholilc hepatitis superimposed on cirrhosis is reversible and predicts the outcome,", Hepatology, 2007, vol. 3, Issue 46, pp. 831-840.

Mouille et al., "Adaptive increase of ornithine production and decrease of ammonia metabolism in rat colonocytes after hyperproteic diet ingestion", Am J Gasteroenterol, 2004, vol. 287, pp. 344-351.

Nance et al., "Ammonia production in germ-free Eck fistula dogs", Surgery, 1971, vol. 70, Issue 2, pp. 169-174.

Navasa et al., "Bacterial infections in liver cirrhosis,", Ital J Gastroenterol Hepatol., 1999, vol. 7, Issue 31, pp. 616-625.

Newsholme et al., "Glutamine metabolism by lymphocytes, macrophages, and neutrophils: its importance in health and disease,", J Nutr Biochem., 1999, vol. 6, Issue 10, pp. 316-324.

Newsholme, "Why is L-glutamine metabolism important to cells of the immune system in health, postinjury, surgery or infection?", J Nutr., 2001, vol. 9 Suppl, Issue 131, pp. 2515S-2522S.

Olde Damink et al., "Decreased plasma and tissue isoleucine levels after simulated gastrointestinal bleeding by blood gavages in chronic portacaval shunted rats", Gut, 1997, vol. 40, pp. 418-424.

Olde Damink et al., "Interorgan ammonia and amino acid metabolism in metabolically stable patients with cirrhosis and a TIPSS", Hepatology, 2002, vol. 36, Issue 5, pp. 1163-1171.

Olde Damink et al., "Interorgan ammonia metabolism in liver failure", [not known], 2002, vol. 41, pp. 177-188.

Olde Damink et al., "The kidney plays a major role in the hyperammonemia seen after simulated or actual GI bleeding in patients with cirrhosis", [not known], 2003, vol. 37, pp. 1277-1285.

Pauwels et al., "Systemic antibiotic prophylaxis after gastrointestinal hemorrhage in cirrhotic patients with a high risk of infection", Hepatology, 1996, vol. 24, Issue 4, pp. 802-806.

Petrowski et al., "Pharmacologic amino acid acylation in the acute hyperammonemia of propionic acidemia", Journal of Neurogenetics, 1987, vol. 4, pp. 87-96.

Plecko et al., "Partial N-acetylglutamate synthetase deficiency in a 13-year-old girl: diagnosis and response to treatment with N-carbamylglutamate", Eur J Pediatr., 1998, vol. 157, pp. 996-998.

Praphanphoj et al., "Three cases of intravenous sodium benzoate and sodium phenylacetate toxicity occurring in the treatment of acute hyperammonaemia", J Inherit Metab Dis., 2000, vol. 23, pp. 129-136.

Rajkovic et al., "Mechanisms of abnormalities in host defences against bacterial infection in liver disease,", Clin Sci. (Lond.), 1985, vol. 3, Issue 68, pp. 247-253.

Ramaswamy et al., "Mouse model for human arginase deficiency", Mol Cell Biol., Jul. 2002, vol. 22, Issue 13, pp. 4491-4498.

Rees et al., "Effect of L-Ornithine-L-Aspartate on patients with and without TIPS undergoing glutamine challenge: a double blind, placebo controlled trial", Gut, 2000, vol. 47, pp. 571-574.

Riordan et al., "Treatment of hepatic encephalopathy", Curr Concepts, 1997, vol. 337, Issue 7, pp. 473-479.

Rogers, Q. R. et al., Deficiency of Pyrroline-5-Carboxylate Synthase in the Intestinal Mucosa of the Cat, The Journal of Nutrition, 1985, pp. 146-150, vol. 115, No. 1.

Romero-Gómez et al., "Intestinal glutaminase activity is increased in liver cirrhosis and correlates with minimal hepatic encephalopathy", Journal of Hepatology, 2004, vol. 41, pp. 49-54.

Rose et al., "L-Ornithine-L-Aspartate in experimental portal-systemic encephalopathy: therapeutic efficacy and mechanism of action", Metabolic Brain Disease, 1998, vol. 13, Issue 2, pp. 147-157.

Rose et al., "L-Ornithine-L-Aspartate lowers plasma and cerebrospinal fluid ammonia and prevents brain edema in rats with acute liver failure", Hepatology, 1999, vol. 30, Issue 3, pp. 636-640.

Rudman, Daniel, et al., Maximal Rates of Excretion and Synthesis of Urea in Normal and Cirrhotic Subjects, The Journal of Clinical Investigation, Sep. 1973, vol. 52, pp. 2241-2249.

Rukmini Devi et al., "Region-specific changes in CNS muscarinic acetylcholine receptors in a rat model of hyperammonemia", Biochem Pharmacol., 1998, vol. 56, Issue 2, pp. 237-241.

Sanyal et al., Portosystemic Encephalopathy After Transjugular Intrahepatic Portosystemic Shunt: Results of a Prospective Controlled Study, Hepatology, 1994, p. 46-55, vol. 20, No. 1, Pt. 1.

Sanyal, A. J., Prediction of Variceal Hemorrhage in Patients with Cirrhosis, UpToDate, Inc., Website (www.uptodate.com), Jan. 2010, UpToDate®.

Sarhan et al., "Effects of inhibition of ornithine aminotransferase on thioactamide-induced hepatogenic encephalopathy", Neurochem Res., 1993, vol. 18, Issue 4, pp. 539-549.

Scaglia et al., "Effect of alternative pathway therapy on branched chain amino acid metabolism in urea cycle disorder patients", Mol Genet Metabolism, 2004, vol. 81, pp. S79-S85.

Search Report dated Apr. 8, 2005 from GB patent application No. 0426142.6.

Search Report dated Feb. 21, 2005 from GB patent application No. 0426141.8.

Sears et al., "Disruption of the blood-brain barrier in hyperammonaemic coma and the pharmacologic effects of dexamethasone and difluoromethyl ornithine", J Neurosci Res., 1985, vol. 14, Issue 2, pp. 255-261.

Seiler et al., "Ornithine aminotransferase activity, liver ornithine concentration and acute ammonia intoxication", Life Sciences, 1989, vol. 45, Issue 11, pp. 1009-1020.

Seiler, "Ornithine aminotransferase, a potential target for the treatment of hyperammonemias", Curr Drug Targets., Sep. 2000, vol. 1, Issue 2, pp. 119-153.

Sen et al., "The pathophysiological basis of acute-on-chronic liver failure", Liver, 2002, vol. 22, Issue Suppl. 2, pp. 5-13.

Shangraw, Robert E. et al., Effect of Liver Disease and Transplantation on Urea Synthesis in Humans: Relationship to Acid-Base Status, Am J Physiol Gastrointest Liver Physiol, 1999, vol. 276, pp. 1145-1152.

Shawcross et al., "Ammonia impairs neutrophil phagocytic function in liver disease," Hepatology, 2008, vol. 4, Issue 48, pp. 1202-1212.

Shawcross et al., "Dispelling myths in the teatment of hepatic encephalopathy," Lancet, 2005, vol. 9457, Issue 365, pp. 431-433.

Shawcross et al., "Hyperammonemia impairs neutrophil function," Hepatology, 2005, vol. 42, p. 537A.

(56) References Cited

OTHER PUBLICATIONS

Shriner, et al., "Recrystallization," in The Systematic Identification of Organic Compounds, (1998), pp. 78-81.
Simell et al., "Waste nitrogen excretion via amino acid acylation: benzoate and phenylacetate in lysinuric protein intolerance", Pediatric Research, 1986, vol. 20, Issue 11, pp. 1117-1121.
Singh, et al., Changing Epidemiology and Predictors of Mortality in Patients With Spontaneous Bacterial Peritonitis at a Liver Transplant Unit, Clinical Microbiology and Infection, Jun. 2003, p. 531-537, vol. 9, No. 6.
Smith et al., "The treatment of inborn errors of the urea cycle", Nature, 1981, vol. 291, Issue 5814, pp. 378-380.
Soláini et al., "Variations in the plasma concentration of ornithine, citrulline and arginine in acute experimental liver failure" [Article in Italian], Boll Soc Ital Biol Sper., 1981, vol. 57, Issue 7, pp. 705-710.
Stedman's Medical Dictionary, "Encephalopathy", 27th Edition (2002), 1 page.
Stewart, P. M., et al., "Effects of Arginine-Free Meals on Ureagenesis in Cats," American Journal of Physiological, 1981, p. E310-E315, vol. 241, No. 4.
Stravitz, MD, et al., Intensive Care of Patients with Acute Liver Failure: Recommendations of the U.S. Acute Liver Failure Study Group, Critical Care Medicine, 2007, p. 2498-2508, vol. 35, No. 11.
Suchy et al., Liver Disease in Children, 2nd Edition, 2001, pp. 74-77.
Sugarbaker et al., "The role of the small intestine in ammonia production after gastric blood administration", Ann Surg., 1987, vol. 206, Issue 1, pp. 5-17.
Sukhotnik et al., "Oral glutamine prevents gut mucosal injury and improves mucosal recovery following lipopolysaccharide endotoxemia in a rat,", J Surg Res., 2007, vol. 2, Issue 143, pp. 379-384.
Svanberg et al., "Effects of amino acids on synthesis and degradation of skeletal muscle proteins in humans", Am J Physiol., 1996, vol. 271, Issue 4 Pt1, pp. E718-E724.
TDRdata.com, results from query of "Spontaneous Bacterial Peritonitis" in the epidemiological and references databases at www.tdrdata.com, retrieved on Jul. 27, 2010, pp. 1-7.
Teran et al., "Primary prophylaxis of variceal bleeding in cirrhosis: A cost-effectiveness analysis", Gastroenter., 1997, vol. 112, Issue 2, pp. 473-482.
Tuchman, M., et al., Management of Inherited Disorders of Ureagenesis, The Endocrinologist, 2002, p. 99-109, vol. 12, No. 2.
Tuchman, MD et al., "Episodic hyperammonemia in adult siblings with hyperornithinemia, hyperammonemia, and homocitrullinuria syndrome", Arch Neurol., 1990, vol. 47, pp. 1134-1137.
Van Berlo et al., "Is increased ammonia liberation after bleeding in the digestive tract the consequence of complete absence of isoleucine in hemoglobin? A study in pigs", Hepatology, 1989, vol. 10, Issue 3, pp. 315-323.
Van Den Berg et al., "The effect of glutamine-enriched enteral nutrition on intestinal microflora in very low birth weight infants: a randomized controlled trial,", Clin Nutr., 2007, vol. 4, Issue 26, pp. 430-439.
Vilstrup, H. et al., Elimination of Infused Amino Acids From Plasma of Control Subjects and of Patients With Cirrhosis of the Liver, European Journal of Clinical Investigation, 1982, vol. 12, pp. 197-202.
Vogels et al., "L-ornithine vs L-ornithine-L-aspartate as a treatment for hyperammonemia-induced encephalopathy in rats", J Hepatology, 1997, vol. 26, Issue 1, pp. 174-182.
Wasmuth et al., "Patients with acute on chronic liver failure display 'sepsis-like' immune paralysis,", J Hepatol., 2005, vol. 2, Issue 42, pp. 195-201.
Written Opinion of the International Preliminary Examining Authority, mailed Mar. 17, 2011, for International Application No. PCT/US2010/029708.
Written Opinion of the International Preliminary Examining Authority, mailed Jun. 2, 2011, for International Application No. PCT/US2010/029708.
Written Opinion of the International Search Authority issued Feb. 7, 2006 of the International Application No. PCT/GB2005/004539.
Ytrebø et al., "Interorgan ammonia, glutamate, and glutamine trafficking in pigs with acute liver failure,", Am J Physiol Gastrointest Liver Physiol., 2006, vol. 3, Issue 291, pp. G373-G381.
Zieve et al., "Ammonia toxicity: comparative protective effect of various arginine and ornithine derivatives, aspartate, benzoate, and carbamyl glutamate", Metabo Brain Dis., 1986, vol. 1, Issue 1, pp. 25-35.
Zieve et al., "Conditional deficiencies of ornithine or ornithine or arginine", J Am Coll Nutr., 1986, vol. 5, Issue 2, pp. 167-176.
Berg et al., "Pharmacokinetics and cerebrospinal fluid penetration of pheylacetate and phenylbutyrate in the non-human primate", Cancer Chemother Pharmacol. (May 2001) 47(5): 385-390. Abstract Only.
Jiang et al., "L-Ornithine-l-aspartate in the management of hepatic encephalopathy: a meta-analysis", J Gastroenterol Hepatol. (2009) 24(1): 9-14; available online: Sep. 28, 2008.
Eurasian Office Action dated Mar. 21, 2014 from Application No. 201390403, filed Apr. 17, 2013.
Chinese Office Action dated Jul. 11, 2014 from Application No. 201080021311.6, filed Apr. 1, 2010.
Singapore Search Report and Written Opinion dated Jul. 11, 2014 from Application No. 201107116-4, filed Apr. 1, 2010.

FIG. 1 X-ray powder diffraction pattern of Form I

FIG. 3  Thermogravimetric Gravimetric/Differential Thermal Analysis of Form I

FIG. 4   $^1$H nuclear magnetic resonance spectrum obtained from Form I

Dynamic Vapor Sorption Results for Form II

FIG. 13  Thermogravimetric Gravimetric/Differential Thermal Analysis of Form III FIG. 14 ¹H nuclear magnetic resonance spectrum obtained from Form III FIG. 19 ¹H nuclear magnetic resonance spectrum obtained from Form V

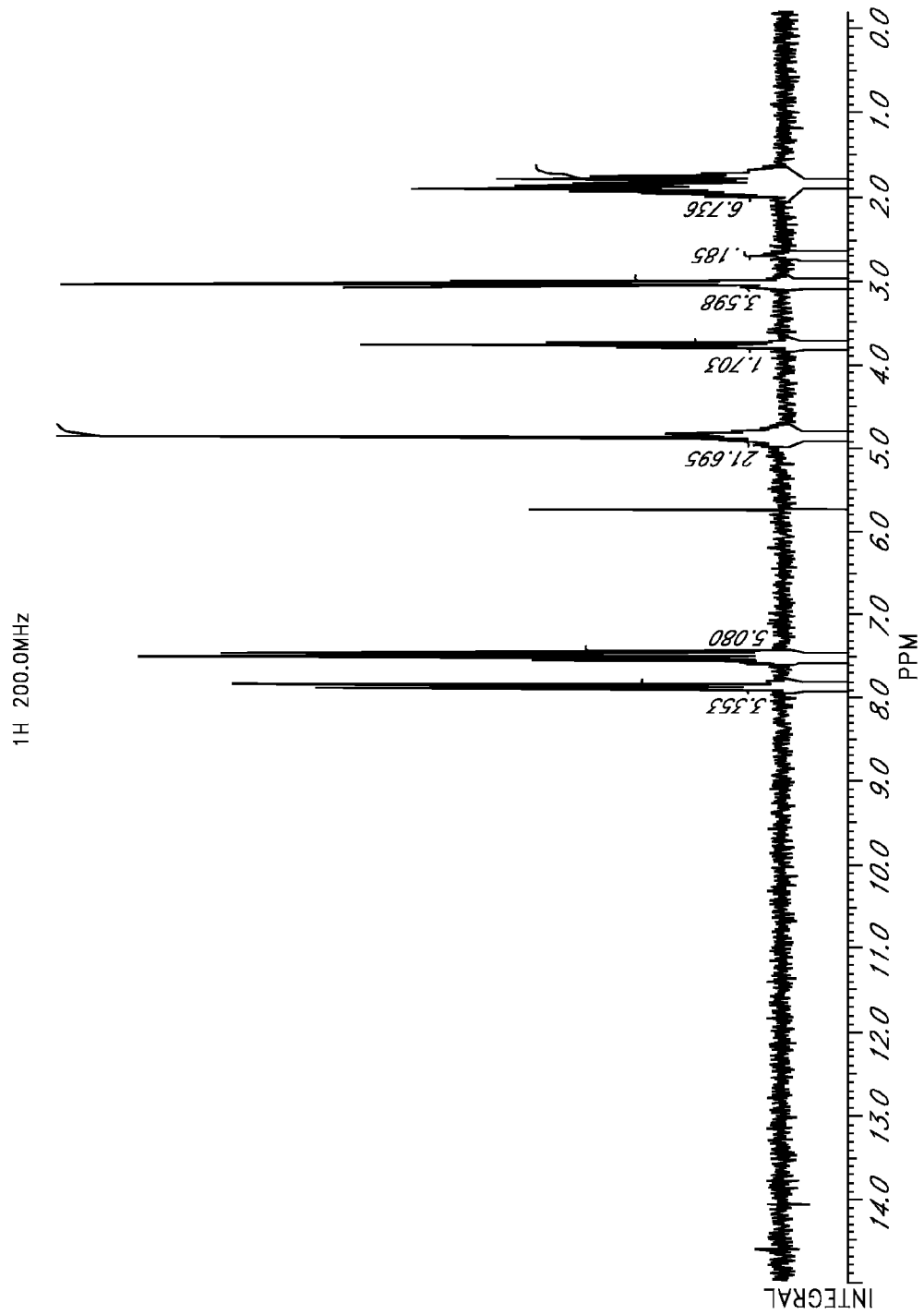
FIG. 21 Representative ¹H Spectra of L-ornithine benzoate

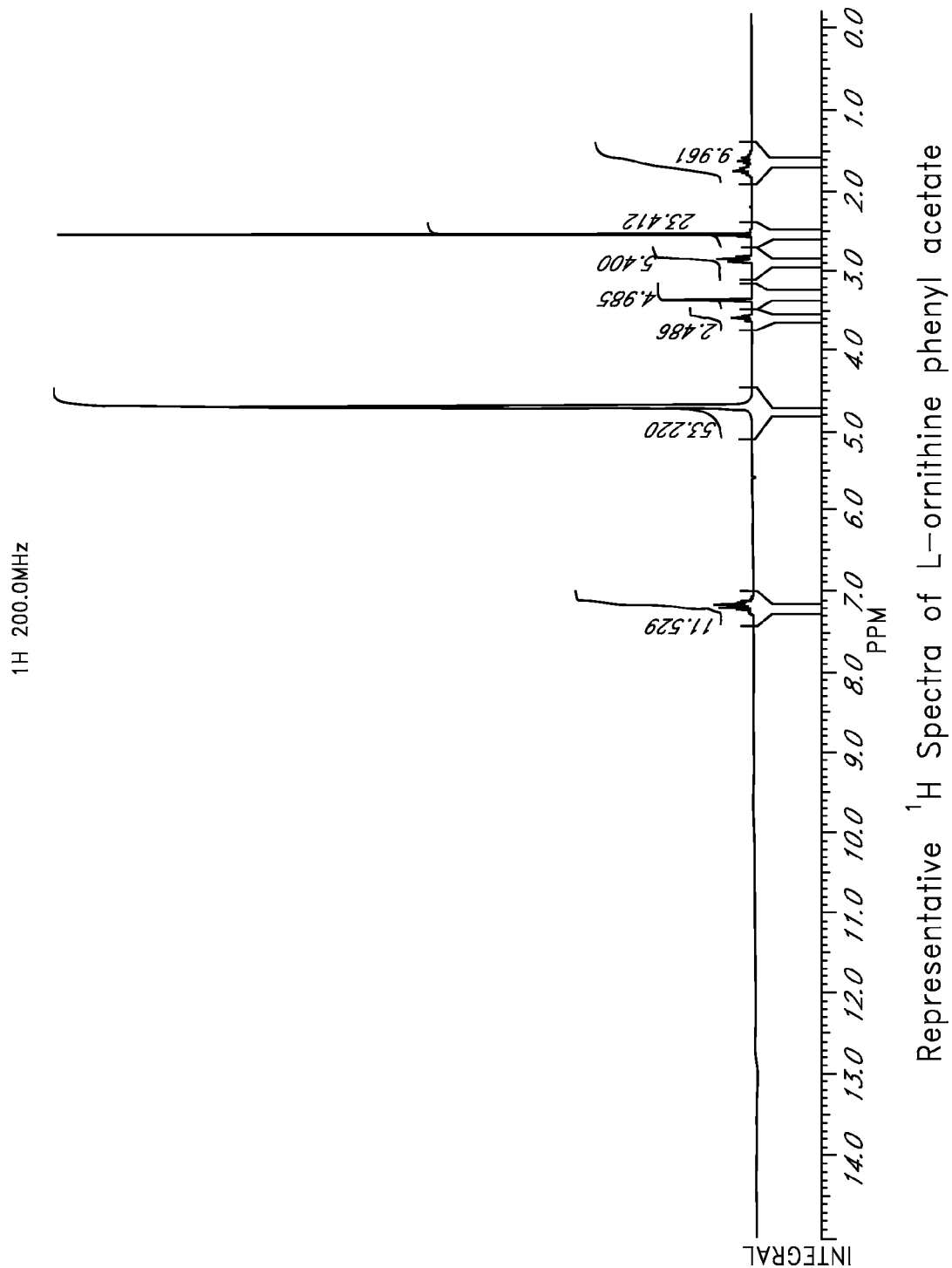
FIG. 22 Representative ¹H Spectra of L-ornithine phenyl acetate

US 8,946,473 B2

METHODS OF MAKING L-ORNITHINE PHENYL ACETATE

INCORPORATION BY REFERENCE TO ANY PRIORITY APPLICATIONS

This application is the U.S. National Phase under 35 U.S.C. §371 of International Application No. PCT/US2011/054983, entitled "METHODS OF MAKING L-ORNITHINE PHENYL ACETATE," filed Oct. 5, 2011, and published in English on Apr. 12, 2012 as WO 2012/048043, which claims the benefit of priority to U.S. Provisional Application No. 61/390,585, filed Oct. 6, 2010, which is hereby incorporated by reference in its entirety. Any and all applications for which a foreign or domestic priority claim is identified in the Application Data Sheet as filed with the present application, or any correction thereto, are hereby incorporated by reference under 37 CFR 1.57.

BACKGROUND

1. Field

The present application relates to the fields of pharmaceutical chemistry, biochemistry, and medicine. In particular, it relates to methods of making L-ornithine phenyl acetate salts.

2. Description

Hyperammonemia is a hallmark of liver disease and is characterized by an excess of ammonia in the bloodstream. Hepatic encephalopathy is a primary clinical consequence of progressive hyperammonemia and is a complex neuropsychiatric syndrome, which may complicate acute or chronic hepatic failure. It is characterized by changes in mental state including a wide range of neuropsychiatric symptoms ranging from minor signs of altered brain function to overt psychiatric and/or neurological symptoms, or even deep coma. The accumulation of unmetabolized ammonia has been considered as the main factor involved in the pathogenesis of hepatic encephalopathy, but additional mechanisms may be associated.

L-Ornithine monohydrochloride and other L-ornithine salts are available for their use in the treatment of hyperammonemia and hepatic encephalopathy. For example, U.S. Publication No. 2008/0119554, which is hereby incorporated by reference in its entirety, describes compositions of L-ornithine and phenyl acetate for the treatment of hepatic encephalopathy. L-ornithine has been prepared by enzymatic conversion methods. For example, U.S. Pat. Nos. 5,405,761 and 5,591,613, both of which are hereby incorporated by reference in their entirety, describe enzymatic conversion of arginine to form L-ornithine salts. Sodium phenyl acetate is commercially available, and also available as an injectable solution for the treatment of acute hyperammonemia. The injectable solution is marketed as AMMONUL.

Although salt forms may exhibit improved degradation properties, certain salts, particularly sodium or chloride salts, may be undesirable when treating patients having diseases associated with the liver disease, such as hepatic encephalopathy. For example, a high sodium intake may be dangerous for cirrhotic patients prone to ascites, fluid overload and electrolyte imbalances. Similarly, certain salts are difficult to administer intravenously because of an increased osmotic pressure, i.e., the solution is hypertonic. High concentrations of excess salt may require diluting large volumes of solution for intravenous administration which, in turn, leads to excessive fluid overload. Accordingly, there exists a need for the preparation of L-ornithine and phenyl acetate salts which are favorable for the treatment of hepatic encephalopathy or other conditions where fluid overload and electrolyte imbalance are prevalent.

SUMMARY

Some embodiments disclosed herein include a process for making L-ornithine phenyl acetate.

Some embodiments disclosed herein include a process for making L-ornithine phenyl acetate salt comprising intermixing an L-ornithine, or a salt thereof, and phenyl acetic acid, or a salt thereof.

Some embodiments include a process for making L-ornithine phenyl acetate salt comprising intermixing a phenyl acetate salt, L-ornithine benzoate, and a solvent; and isolating a composition comprising at least 70% crystalline L-ornithine phenyl acetate by weight.

In some embodiments, the process further includes forming L-ornithine benzoate by intermixing an L-ornithine salt, a benzoate salt and a first solvent to form an intermediate solution.

In some embodiments, the process further includes removing at least a portion of a salt from said intermediate solution before intermixing the phenyl acetate salt, wherein said salt is not an L-ornithine salt.

In some embodiments, the salt removed from the intermediate solution comprises an anion derived at least in part from the L-ornithine salt and a cation derived at least in part from the benzoate salt.

In some embodiments, the L-ornithine salt is L-ornithine hydrochloride and said anion is chloride.

In some embodiments, the benzoate salt is silver benzoate and the cation is a silver ion.

In some embodiments, the process further comprises adding hydrochloric acid before removing at least a portion of the salt.

In some embodiments, at least about 90% by weight of the salt is removed from the intermediate solution.

In some embodiments, the process further comprises forming L-ornithine benzoate by intermixing an L-ornithine salt, a benzoate salt and a solvent to form an intermediate solution, and isolating L-ornithine benzoate from said intermediate solution.

In some embodiments, the process further comprises removing at least a portion of a salt from the intermediate solution before isolating the L-ornithine benzoate, wherein the salt is not an L-ornithine salt.

In some embodiments, the process further comprises adding hydrochloric acid before removing at least a portion of the salt.

In some embodiments, the isolation of L-ornithine benzoate comprises crystallizing L-ornithine benzoate from the intermediate solution.

In some embodiments, the phenyl acetate salt is dispersed in a solution which is intermixed with L-ornithine benzoate and the solvent.

Some embodiments include a process for making L-ornithine phenyl acetate salt comprising: preparing a solution of phenyl acetate salt by mixing a phenyl acetic acid and an appropriate base in a first solvent; intermixing an L-ornithine benzoate with the solution of phenyl acetate salt; and isolating a composition comprising L-ornithine phenyl acetate.

In some embodiments, the appropriate base is selected from the group consisting of an alkali metal hydroxide and an alkali metal alkoxide.

In some embodiments, the process further comprises forming L-ornithine benzoate by intermixing an L-ornithine salt, a benzoate salt and a second solvent to form an intermediate solution.

In some embodiments, the composition comprises at least about 0.10% by weight benzoate salt.

In some embodiments, the composition comprises no more than 5% by weight benzoate salt.

In some embodiments, the composition comprises no more than 3% by weight benzoate salt.

In some embodiments, the composition comprises no more than 1% by weight benzoate salt.

In some embodiments, the L-ornithine salt is L-ornithine hydrochloride.

In some embodiments, the benzoate salt is silver benzoate.

In some embodiments, the composition further comprises at least 10 ppm silver.

In some embodiments, the composition comprises at least 20 ppm silver.

In some embodiments, the composition comprises at least 25 ppm silver.

In some embodiments, the composition comprises no more than 600 ppm silver.

In some embodiments, the composition comprises no more than 100 ppm silver.

In some embodiments, the composition comprises no more than 65 ppm silver.

In some embodiments, the phenyl acetate is an alkali metal salt.

In some embodiments, the alkali metal salt is sodium phenyl acetate.

In some embodiments, the composition comprises no more than 100 ppm sodium.

In some embodiments, the composition comprises no more than 20 ppm sodium.

In some embodiments, the L-ornithine salt is a halide salt.

In some embodiments, the L-ornithine halide salt is L-ornithine hydrochloride.

In some embodiments, the composition comprises no more than 0.1% by weight chloride.

In some embodiments, the composition comprises no more than 0.01% by weight chloride.

Some embodiments include a process for making L-ornithine phenyl acetate salt comprising: increasing the pH value of a mixture comprising an L-ornithine salt at least until an intermediate salt precipitates, wherein said intermediate salt is not an L-ornithine salt; isolating the intermediate salt from said mixture; intermixing phenyl acetic acid with said mixture; and isolating L-ornithine phenyl acetate salt from said solution.

In some embodiments, the pH value is increased to at least 8.0.

In some embodiments, the pH value is increased to at least 9.0.

In some embodiments, increasing the pH value comprises adding a pH modifier selected from the group consisting of sodium hydroxide, potassium hydroxide, cesium hydroxide, lithium hydroxide, calcium hydroxide, magnesium hydroxide, barium hydroxide, ammonium hydroxide, sodium carbonate, sodium bicarbonate, potassium carbonate, potassium bicarbonate, calcium carbonate, magnesium carbonate, barium carbonate, sodium methoxide, potassium t-butoxide, dibutylamine, tryptamine, lithium hydride, sodium hydride, calcium hydride, butyl lithium, ethyl magnesium bromide or combinations thereof.

In some embodiments, the intermediate salt comprises an anion derived at least in part from the L-ornithine salt.

In some embodiments, the intermediate salt comprises a cation derived at least in part from the pH modifier.

In some embodiments, the pH modifier is selected from the group consisting of sodium hydroxide, sodium methoxide, calcium hydroxide, calcium carbonate and barium hydroxide.

Some embodiments include a process for making L-ornithine phenyl acetate salt comprising intermixing an L-ornithine salt, a phenyl acetate salt and a solvent to form a solution, and isolating L-ornithine phenyl acetate from said solution.

In some embodiments, the L-ornithine salt is a halide salt. In some embodiments, the halide salt is not L-ornithine hydrochloride.

In some embodiments, the phenyl acetate salt is silver phenyl acetate.

In some embodiments, the L-ornithine salt is L-ornithine hydrochloride.

Some embodiments include compositions of L-ornithine phenyl acetate prepared according to the methods disclosed herein.

BRIEF DESCRIPTION OF THE DRAWINGS

FIG. 21 shows the $^1$H nuclear magnetic resonance spectrum obtained from a sample of L-ornithine benzoate.

FIG. 22 shows the 1H nuclear magnetic resonance spectrum obtained from a sample of L-ornithine phenyl acetate.

DETAILED DESCRIPTION

Figure 1:
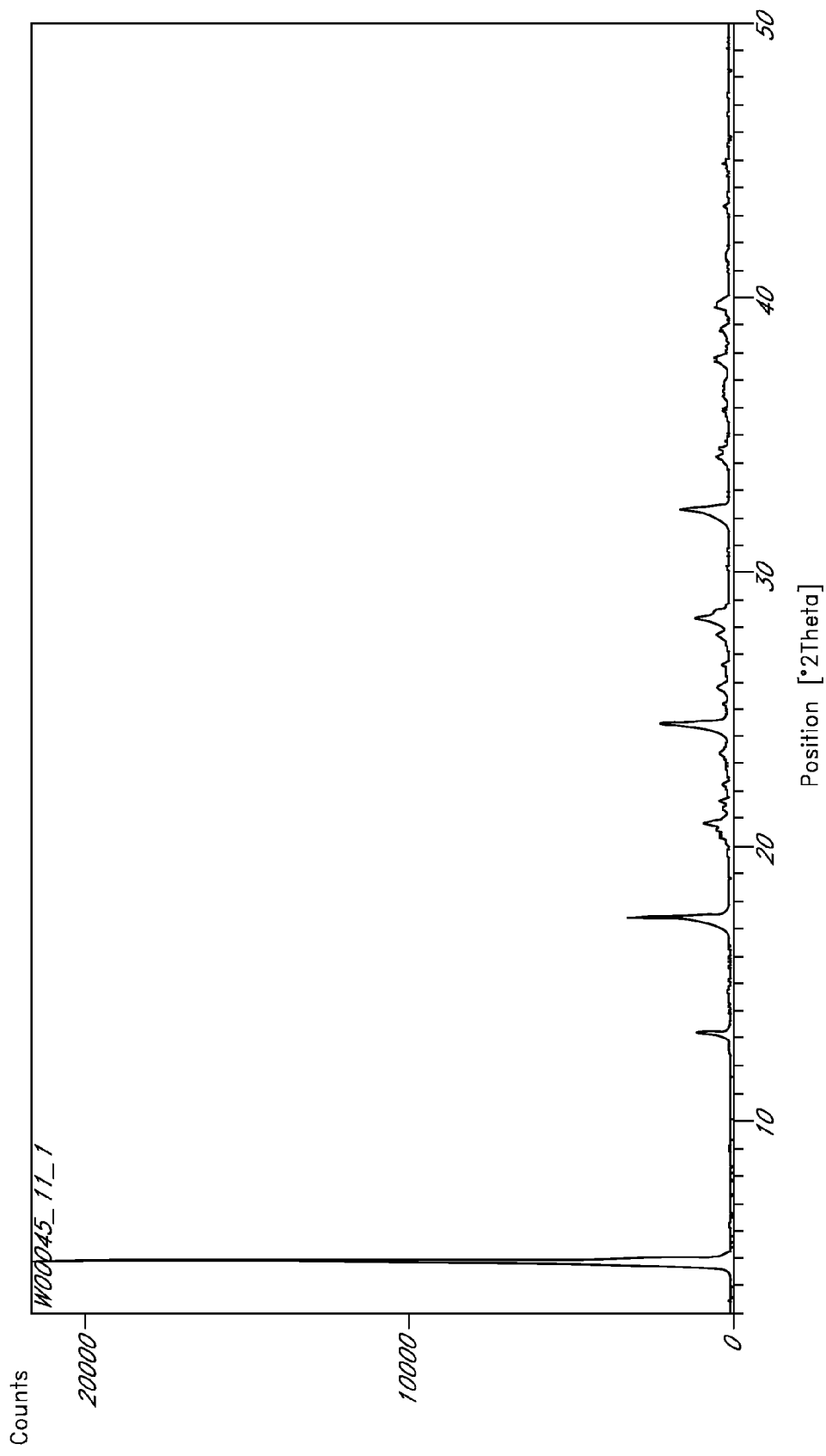
FIG. 1 is an X-ray powder diffraction pattern of Form I.

Some embodiments disclosed herein include a method of making L-ornithine phenyl acetate salt. L-Ornithine phenyl acetate may be produced, for example, through an intermediate salt, such as L-ornithine benzoate. As shown in Scheme 1, an L-ornithine salt of Formula I can be reacted with a benzoate salt of Formula II to obtain the intermediate L-ornithine benzoate.

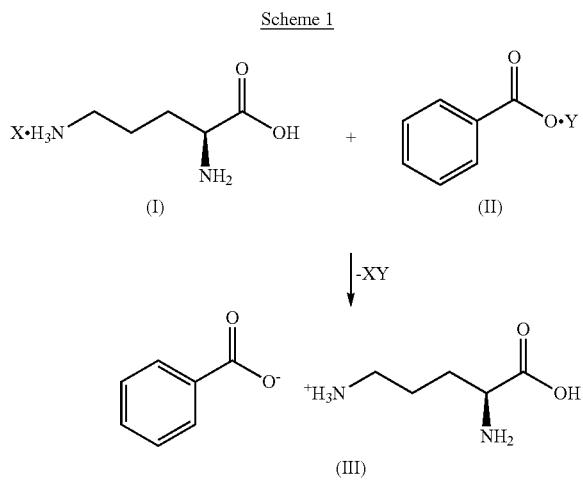

Scheme 1

Various salts of L-ornithine may be used in the compound of Formula I, and therefore X in Formula I can be any ion capable of forming a salt with L-ornithine other than benzoic acid or phenyl acetic acid. X can be a monoatomic anion, such as, but not limited to, a halide (e.g., fluoride, chloride, bromide, and iodide). X can also be a polyatomic anion, such as, but not limited to, acetate, aspartate, formate, oxalate, bicarbonate, carbonate, sulfate, nitrate, isonicotinate, salicylate, citrate, tartrate, pantothenate, bitartrate, ascorbate, succinate, maleate, gentisinate, fumarate, gluconate, glucaronate, saccharate, glutamate, methanesulfonate, ethanesulfonate, benzensulfonate, p-toluenesulfonate, pamoate (i.e., 1,1'-methylene-bis-(2-hydroxy-3-naphthoate), phosphate and the like. X may be an organic or inorganic group. In some embodiments, X is a monovalent ion. In some embodiments, X is chloride.

Similarly, the benzoate salt of Formula II is not particularly limited, and therefore Y in Formula II can be any appropriate ion capable of forming a salt with benzoic acid. In some embodiments, Y can be a monoatomic cation, such as an alkali metal ion (e.g., $Li^+$, $Na^+$, and $K^+$) and other monovalent ions (e.g., $Ag^+$). Y may also be a polyatomic cation, such as ammonium, L-arginine, diethylamine, choline, ethanolamine, 1H-imidazole, trolamine, and the like. In some embodiments, Y is an inorganic ion. In some embodiments, Y is silver.

Many other possible salts of L-ornithine and benzoic acid may be used for the compounds of Formulae I and II, respectively, and can readily be prepared by those skilled in the art. See, for example, Bighley L. D., et al., "Salt forms of drugs and absorption," In: Swarbrick J., Horlan J. C., eds. Encyclopedia of pharmaceutical technology, Vol. 12. New York: Marcel Dekker, Inc. pp. 452-499, which is hereby incorporated by reference in its entirety.

The intermediate L-ornithine benzoate (i.e., Formula III) can be prepared by intermixing solutions including compounds of Formulae I and II. As an example, the compounds of Formulae I and II may be separately dissolved in water and dimethyl sulfoxide (DMSO), respectively. The two solutions may then be intermixed so that the L-ornithine and benzoic acid react to form the salt of Formula III. Alternatively, the two salt compounds can be directly dissolved into a single solution. In some embodiments, L-ornithine and benzoic acid are dissolved in separate solvents, and subsequently intermixed. In some embodiments, L-ornithine is dissolved in an aqueous solution, benzoic acid is dissolved in an organic solvent, and the L-ornithine and benzoic acid solutions are subsequently intermixed.

Non-limiting examples of solvents which may be used when intermixing L-ornithine and benzoate salts include acetonitrile, dimethylsulfoxide (DMSO), cyclohexane, ethanol, acetone, acetic acid, 1-propanol, dimethylcarbonate, N-methyl-2-pyrrolidone (NMP), ethyl acetate (EtOAc), toluene, isopropyl alcohol (IPA), diisopropyl ether, nitromethane, water, 1,4-dioxane, diethyl ether, ethylene glycol, methyl acetate (MeOAc), methanol, 2-butanol, cumene, ethyl formate, isobutyl acetate, 3-methyl-1-butanol, anisole, and combinations thereof. In some embodiments, the L-ornithine benzoate solution includes water. In some embodiments, the L-ornithine benzoate solution includes DMSO.

Upon intermixing L-ornithine and benzoate salts, counterions X and Y may form a precipitate that can be removed from the intermixed solution using known methods, such as filtration, centrifugation, and the like. In some embodiments, X is chloride, Y is silver, and the reaction produces a precipitate having AgCl. Although Scheme 1 shows the compounds of Formulae I and II as salts, it is also within the scope of the present application to intermix the free base of L-ornithine and benzoic acid to form the intermediate of L-ornithine benzoate. Consequently, forming and isolating the precipitate is optional.

The relative amount of L-ornithine and benzoate salts that are intermixed is not limited; however the molar ratio of L-ornithine to benzoic acid may optionally be in the range of about 10:90 and 90:10. In some embodiments, the molar ratio of L-ornithine benzoate can be in the range of about 30:70 and 70:30. In some embodiments, the molar ratio of L-ornithine to benzoate can be in the range of about 40:60 and 60:40. In some embodiments, the molar ratio of L-ornithine to benzoate is about 1:1.

In embodiments where X and Y are both inorganic ions (e.g., X and Y are chloride and silver, respectively), additional amounts of X-containing salt may be added to encourage further precipitation of the counterion Y. For example, if X is chloride and Y is silver, the molar ratio of L-ornithine hydrochloride to silver benzoate may be greater than 1:1 so that an excess of chloride is present relative to silver. Accordingly, in some embodiments, the molar ratio of L-ornithine to benzoic acid is greater than about 1:1. Nevertheless, the additional chloride salt is not required to be derived from an L-ornithine salt (e.g., L-ornithine hydrochloride). For example, dilute solutions of hydrochloric acid may be added to the solution to further remove silver. Although it is not particularly limited when the additional X-containing salt is added, it is preferably added before the AgCl is initially isolated.

As shown in Scheme 2, the L-ornithine benzoate can react with a phenyl acetate salt of Formula IV to form L-ornithine phenyl acetate. For example, sodium phenyl acetate can be intermixed with a solution of L-ornithine benzoate to form L-ornithine phenyl acetate. Various salts of phenyl acetate may be used, and therefore Z in Formula IV can be any cation capable of forming a salt with phenyl acetate other than benzoic acid or L-ornithine. In some embodiments, Z can be a monoatomic cation, such as an alkali metal ion (e.g., $Li^+$, $Na^+$, and $K^+$) and other monovalent ions (e.g., $Ag^+$). Z may also be a polyatomic cation, such as ammonium, L-arginine, diethylamine, choline, ethanolamine, 1H-imidazole, trolamine, and the like. In some embodiments, Z is an inorganic ion. In some embodiments, Z is sodium.

The phenyl acetate salt may optionally be prepared in solution using phenyl acetic acid and an appropriate base. This solution may be intermixed with L-ornithine benzoate to obtain L-ornithine phenyl acetate as described above. As an example, phenyl acetic acid may be intermixed with sodium hydroxide in isopropanol to obtain a solution of sodium phenyl acetate. The solution of sodium phenyl acetate can then be intermixed with a solution of L-ornithine benzoate. Alternatively, the phenyl acetate salt may optionally be isolated as a solid before intermixing with L-ornithine benzoate.

The base for preparing phenyl acetate salt is not particularly limited and will be selected, in part, based upon the desired phenyl acetate salt. As an example, sodium phenyl acetate may be obtained by adding sodium hydroxide or sodium methoxide. The base can be an inorganic base or an organic base. In some embodiments, the base is an alkali metal base. For example, the base may include lithium hydroxide, sodium hydroxide, and potassium hydroxide. In some embodiments, the base is an alkaline earth metal salt. As an example, the base may include calcium hydroxide, magnesium hydroxide, and barium hydroxide. In some embodiments, the base is water-soluble. Non-limiting examples of bases include sodium hydroxide, potassium hydroxide, calcium hydroxide, magnesium hydroxide, sodium methoxide, potassium methoxide, calcium methoxide, magnesium methoxide, sodium tert-butoxide, potassium tert-butoxide, calcium tert-butoxide, and magnesium tert-butoxide The relative amount of L-ornithine salt and phenyl acetate salt that are intermixed is also not limited; however the molar ratio of L-ornithine to phenyl acetate may optionally be in the range of about 10:90 and 90:10. In some embodiments, the molar ratio of L-ornithine to phenyl acetate can be in the range of about 30:70 and 70:30. In some embodiments, the molar ratio of L-ornithine to phenyl acetate can be in the range of about 40:60 and 60:40. In some embodiments, the molar ratio of L-ornithine to phenyl acetate is about 1:1.

Scheme 2

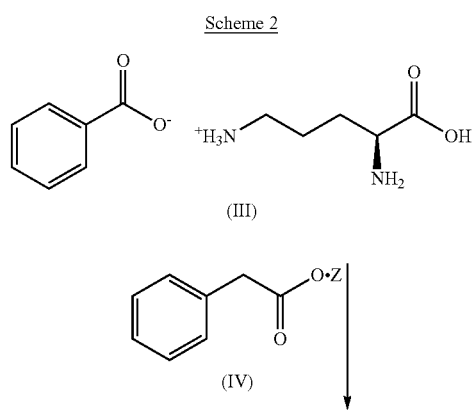

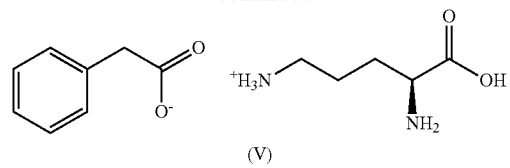

The L-ornithine phenyl acetate of Formula V may then be isolated from solution using known techniques. For example, by evaporating any solvent until the L-ornithine phenyl acetate crystallizes, or alternatively by the adding an anti-solvent miscible in the L-ornithine phenyl acetate solution until the L-ornithine phenyl acetate precipitates from solution. Another possible means for isolating the L-ornithine phenyl acetate is to adjust the temperature of the solution (e.g., lower the temperature) until the L-ornithine phenyl acetate precipitates.

The method of isolating the L-ornithine phenyl acetate affects the crystalline form that is obtained. The crystalline forms are discussed further below and are also disclosed in three related applications: (i) U.S. Provisional Application No. 61/166,676, filed Apr. 3, 2009; (ii) PCT/US2010/029708, filed in English on Apr. 1, 2010; and (iii) U.S. application Ser. No. 12/753,763, filed Apr. 2, 2010. These applications are hereby incorporated by reference in their entirety.

The isolated L-ornithine phenyl acetate may be subjected to various additional processing, such as drying and the like. In some embodiments, L-ornithine phenyl acetate may be subsequently intermixed with a dilute HCl solution to precipitate residual silver. The L-ornithine phenyl acetate may again be isolated from solution using similar methods disclosed above.

As would be appreciated by a person of ordinary skill in the art, guided by the teachings of the present application, L-ornithine phenyl acetate may similarly be prepared using an intermediate salt other than L-ornithine benzoate. Thus, for example, L-ornithine, or a salt thereof (e.g., L-ornithine hydrochloride), can be intermixed with a solution having acetic acid. L-Ornithine acetate may then be intermixed with phenyl acetic acid, or a salt thereof (e.g., sodium phenyl acetate), to obtain L-ornithine phenyl acetate. Scheme 3 illustrates one example of a process for forming L-ornithine phenyl acetate using L-ornithine acetate as an intermediate salt.

Other salts may be used besides benzoate and acetate. In some embodiments, the intermediate salt can be a pharmaceutically acceptable salt of L-ornithine. For example, the intermediate L-ornithine salt can be an acetate, aspartate, formate, oxalate, bicarbonate, carbonate, sulfate, nitrate, isonicotinate, salicylate, citrate, tartrate, pantothenate, bitartrate, ascorbate, succinate, maleate, gentisinate, fumarate, gluconate, glucaronate, saccharate, benzoate, glutamate, methanesulfonate, ethanesulfonate, benzensulfonate, p-toluenesulfonate, pamoate (i.e., 1,1'-methylene-bis-(2-hydroxy-3-naphthoate) or phosphate. The free acid of the intermediate is preferably a weaker acid relative to phenyl acetic acid. In some embodiments, the intermediate is an L-ornithine salt with an anion component that exhibits a $pK_a$ value that is higher than the $pK_a$ value of phenyl acetic acid. As an example, for L-ornithine acetate, acetic acid and phenyl acetic acid exhibit $pK_a$ values of about 4.76 and 4.28, respectively.

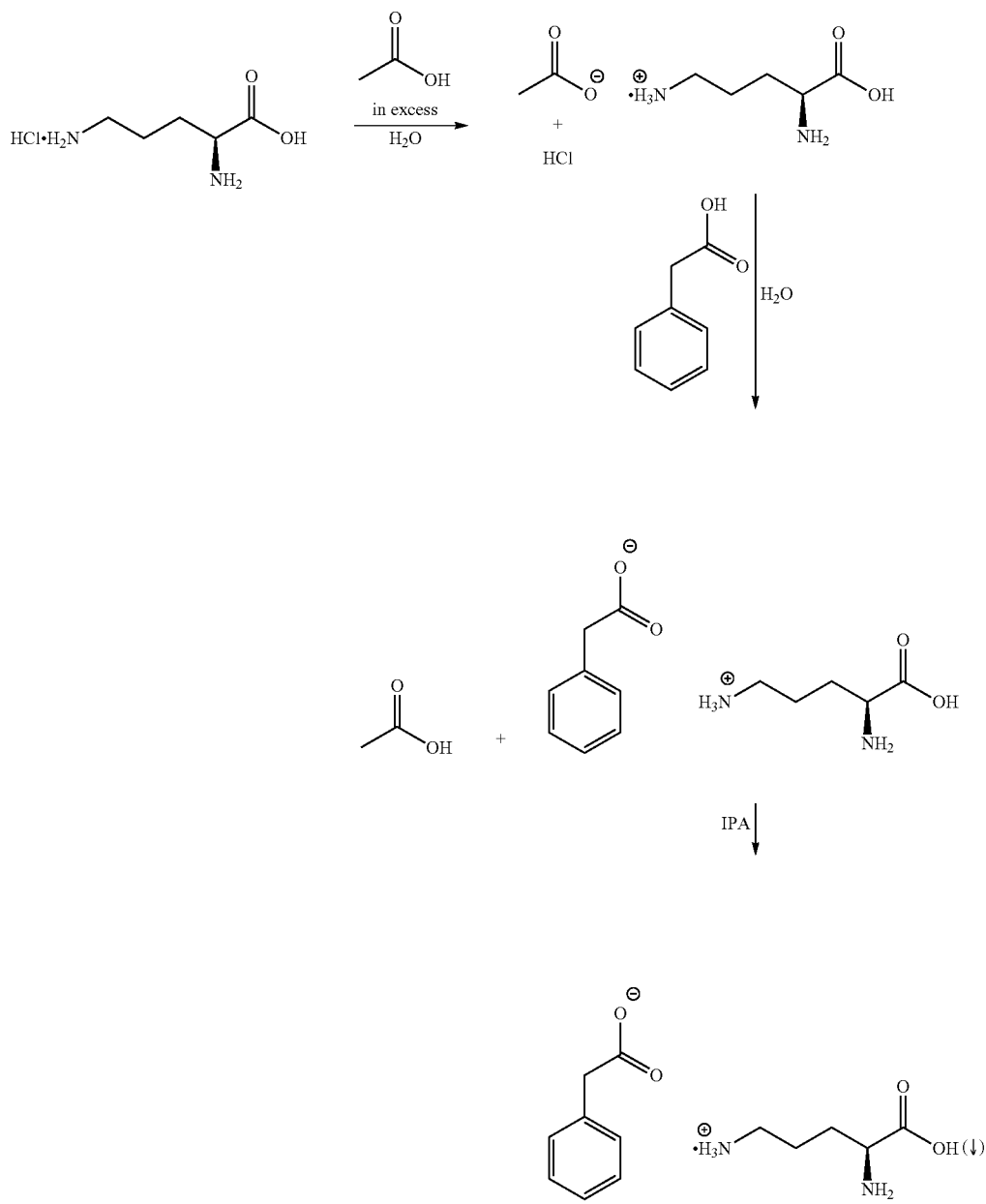

L-Ornithine phenyl acetate may also be prepared, in some embodiments, without forming an intermediate salt, such as L-ornithine benzoate. Scheme 4 illustrates an exemplary process for preparing L-ornithine phenyl acetate without an intermediate salt. A pH modifier may be added to a solution of L-ornithine salt (e.g., as illustrated in Scheme 4 by the compound of Formula I) until a salt precipitates from solution, where the salt is not an L-ornithine salt. As an example, sodium methoxide (NaOMe) can be added to a mixture of L-ornithine hydrochloride until sodium chloride precipitates from solution to leave a free base of L-ornithine. The precipitate may optionally be isolated from solution using known techniques, such as filtration, centrifugation, and the like. The free base of L-ornithine (e.g., as illustrated in Scheme 4 by the compound of Formula I-a) may be intermixed with phenyl acetic acid, or a salt thereof (e.g., as illustrated in Scheme 4 by the compound of Formula IV), to obtain L-ornithine phenyl acetate. The L-ornithine phenyl acetate of Formula V may then be isolated as previously described.

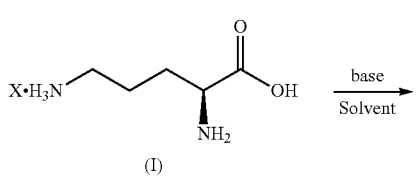

Scheme 4

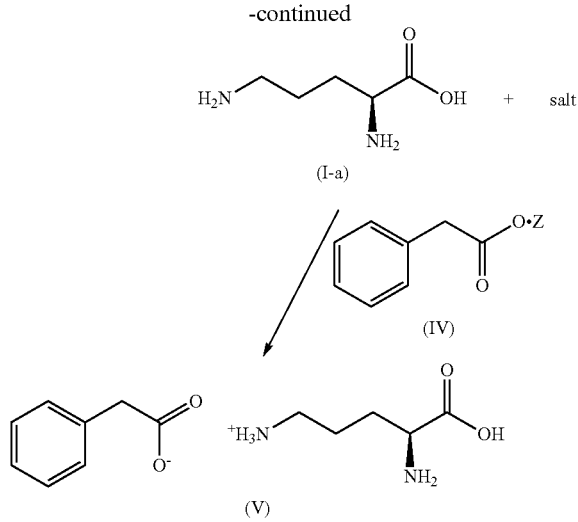

(I-a)

(IV)

(V)

A pH modifier can include a basic compound, or anhydrous precursor thereof, and/or a chemically protected base. Non-limiting examples of pH modifiers include sodium hydroxide, potassium hydroxide, cesium hydroxide, lithium hydroxide, calcium hydroxide, magnesium hydroxide, barium hydroxide, ammonium hydroxide, sodium carbonate, sodium bicarbonate, potassium carbonate, potassium bicarbonate, calcium carbonate, magnesium carbonate, barium carbonate, sodium methoxide, potassium methoxide, sodium t-butoxide, potassium t-butoxide, dibutylamine, tryptamine, lithium hydride, sodium hydride, calcium hydride, butyl lithium, ethyl magnesium bromide and combinations thereof. Also, the amount of pH modifier to be added is not particularly limited; however the molar ratio of L-ornithine to pH modifier may optionally be in the range of about 10:90 and 90:10. In some embodiments, the molar ratio of L-ornithine to pH modifier can be in the range of about 30:70 and 70:30. In some embodiments, the molar ratio of L-ornithine to pH modifier can be in the range of about 40:60 and 60:40. In some embodiments, the molar ratio of L-ornithine to pH modifier is about 1:1. The pH modifier may, in some embodiments be added to adjust the pH value to at least about 8.0; at least about 9.0; or at least about 9.5.

Another process for forming L-ornithine phenyl acetate, in some embodiments, includes reacting a halide salt of L-ornithine with silver phenyl acetate (Scheme 5). As an example, L-ornithine hydrochloride may be intermixed with silver phenyl acetate and a solvent. AgCl may then precipitate and is optionally isolated from the solution. The remaining L-ornithine phenyl acetate can also be isolated using known methods. This process can be completed using generally the same procedures and conditions outlined above.

The relative amount of L-ornithine salt and phenyl acetate salt that are intermixed is also not limited; however the molar ratio of L-ornithine to phenyl acetate may optionally be in the range of about 10:90 and 90:10. In some embodiments, the molar ratio of L-ornithine to phenyl acetate can be in the range of about 30:70 and 70:30. In some embodiments, the molar ratio of L-ornithine to phenyl acetate can be in the range of about 40:60 and 60:40. In some embodiments, the molar ratio of L-ornithine to phenyl acetate is about 1:1.

The L-ornithine phenyl acetate may then be isolated from solution using known techniques. For example, by evaporating any solvent until the L-ornithine phenyl acetate crystallizes, or alternatively by the adding an anti-solvent miscible in the L-ornithine phenyl acetate solution until the L-ornithine phenyl acetate precipitates from solution. Another possible means for isolating the L-ornithine phenyl acetate is to adjust the temperature of the solution (e.g., lower the temperature) until the L-ornithine phenyl acetate precipitates.

Scheme 5

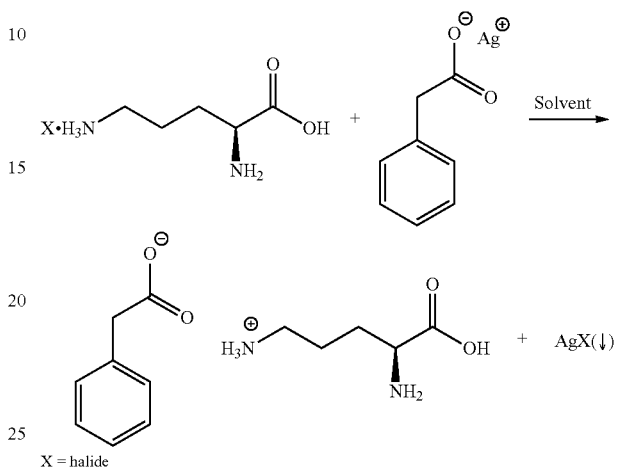

X = halide

The compositions obtained according to the methods disclosed herein can be processed into various forms (e.g., crystalline Form 2, amorphous, etc.) as discussed further below. And the composition can be formulated for various routes of administration. In some embodiments, the compositions can be used to treating or ameliorating hyperammonemia or hepatic encephalopathy.

Compositions of L-Ornithine Phenyl Acetate

Also disclosed herein are compositions of L-ornithine phenyl acetate that may be formed by the process disclosed herein. The compositions of the present application advantageously have low amounts of inorganic salts, particularly alkali metal salts and/or halide salts, and therefore are particularly suited for oral and/or intravenous administration to patients with hepatic encephalopathy. Meanwhile, these compositions may exhibit similar stability profiles compared to other salts (e.g., mixtures of L-ornithine hydrochloride and sodium phenyl acetate). The compositions may, in some embodiments, be obtained by one of the processes disclosed in the present application. For example, any of the disclosed processes using L-ornithine benzoate as an intermediate may yield the compositions of the present application.

The compositions, in some embodiments, can include a crystalline form of L-ornithine phenyl acetate (e.g., Forms I, II, III and/or V disclosed herein). In some embodiments, the composition may include at least about 20% by weight of a crystalline form of L-ornithine phenyl acetate (preferably at least about 50% by weight, and more preferably at least about 80% by weight). In some embodiments, the composition consists essentially of a crystalline form of L-ornithine phenyl acetate. In some embodiments, the composition includes a mixture of at least two (e.g., two, three or four forms) of Forms I, II, III, and V.

The compositions, in some embodiments, include Form II. For example, the compositions may include at least about 20%; at least about 50%; at least about 90%; at least about 95%; or at least about 99% of Form II. Similarly, the compositions may also include, for example, Forms I, III or V. The compositions may optionally include at least about 20%; at least about 50%; at least about 90%; at least about 95%; or at least about 99% of Forms I, II, III and/or V.

Also within the scope of the present application are amorphous forms of L-ornithine phenyl acetate. Various methods are known in the art for preparing amorphous forms. For example, a solution of L-ornithine phenyl acetate may be dried under vacuum by lyophilization to obtain an amorphous composition. See P.C.T. Application WO 2007/058634, which published in English and designates the U.S., and is hereby incorporated by reference for disclosing methods of lyophilization.

It is preferred that the composition have low amounts (if any) of alkali and halogen ions or salts, particular sodium and chloride. In some embodiments, the composition comprises no more than about 100 ppm of alkali metals (preferably no more than about 20 ppm, and most preferably no more than about 10 ppm). In some embodiments, the composition comprises no more than about 100 ppm of sodium (preferably no more than about 20 ppm, and most preferably no more than about 10 ppm). In some embodiments, the composition comprises no more than about 0.1% by weight of halides (preferably no more than about 0.01% by weight). In some embodiments, the composition comprises no more than about 0.1% by weight of chloride (preferably no more than about 0.01% by weight).

The reduced content of alkali metals and halides provides a composition suitable for preparing concentrated isotonic solutions. As such, these compositions can be more easily administered intravenously compared to, for example, administering mixtures of L-ornithine hydrochloride and sodium phenyl acetate. In some embodiments, an about 45 to about 55 mg/mL solution of L-ornithine phenyl acetate in water (preferably about 50 mg/mL) is isotonic with body fluids (e.g., the solution exhibits an osmolality in the range of about 280 to about 330 mOsm/kg).

The compositions may also include residual amounts of the anion from an intermediate salt formed during the process of making the L-ornithine phenyl acetate composition. For example, some of the processes disclosed herein yield compositions having benzoic acid or a salt thereof. In some embodiments, the composition comprises at least about 0.01% by weight benzoic acid or a salt thereof (preferably at least about 0.05% by weight, and more preferably about 0.1% by weight). In some embodiments, the composition comprises no more than about 3% by weight benzoic acid or a salt thereof (preferably no more than about 1% by weight, and more preferably no more than about 0.5% by weight). In some embodiments, the composition includes a salt, or an acid thereof, in the range of about 0.01% to about 3% by weight (preferably about 0.1% to about 1%), wherein the salt is selected from acetate, aspartate, formate, oxalate, bicarbonate, carbonate, sulfate, nitrate, isonicotinate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate, pamoate (i.e., 1,1'-methylene-bis-(2-hydroxy-3-naphthoate) or phosphate.

Similarly, a composition prepared using an acetate intermediate may have residual amounts of acetic acid or acetate. In some embodiments, the composition includes at least about 0.01% by weight acetic acid or acetate (preferably at least about 0.05% by weight, and more preferably about 0.1% by weight). In some embodiments, the composition includes no more than about 3% by weight acetic acid or acetate (preferably no more than about 1% by weight, and more preferably no more than about 0.5% by weight).

The compositions may also include low amounts of silver. Exemplary processes disclosed herein utilize, for example, silver benzoate, but still yield compositions with surprisingly low amounts of silver. Thus, in some embodiments, the composition includes no more than about 600 ppm silver (preferably no more than about 100 ppm, and more preferably no more than about 65 ppm). In some embodiments, the composition includes at least about 10 ppm silver (alternatively at least about 20 or 25 ppm silver).

Pharmaceutical Compositions

The compositions of L-ornithine phenyl acetate prepared by the processes disclosed above may also be formulated for administration to a subject (e.g., a human). L-Ornithine phenyl acetate, and accordingly the compositions disclosed herein, may be formulated for administration with a pharmaceutically acceptable carrier or diluent. L-ornithine phenyl acetate may thus be formulated as a medicament with a standard pharmaceutically acceptable carrier(s) and/or excipient(s) as is routine in the pharmaceutical art. The exact nature of the formulation will depend upon several factors including the desired route of administration. Typically, L-ornithine phenyl acetate is formulated for oral, intravenous, intragastric, subcutaneous, intravascular or intraperitoneal administration.

The pharmaceutical carrier or diluent may be, for example, water or an isotonic solution, such as 5% dextrose in water or normal saline. Solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, gum arabic, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manners, for example, by means of mixing, granulating, tabletting, sugar-coating, or film-coating processes.

Liquid dispersions for oral administration may be syrups, emulsions or suspensions. The syrups may contain as carriers, for example, saccharose or saccharose with glycerine and/or mannitol and/or sorbitol.

Suspensions and emulsions may contain a carrier, for example a natural gum, agar, sodium alginate, pectin, methylcellulose, carboxymethylcellulose, or polyvinyl alcohol. The suspensions or solutions for intramuscular injections may contain, together with L-ornithine phenyl acetate, a pharmaceutically acceptable carrier, e.g. sterile water, olive oil, ethyl oleate, glycols, e.g. propylene glycol, and if desired, a suitable amount of lidocaine hydrochloride.

The medicament may consist essentially of L-ornithine phenyl acetate and a pharmaceutically acceptable carrier. Such a medicament therefore contains substantially no other amino acids in addition to L-ornithine and phenyl acetate. Furthermore, such a medicament contains insubstantial amounts of other salts in addition to L-ornithine phenyl acetate.

Oral formulations may generally include dosages of L-ornithine phenyl acetate in the range of about 500 mg to about 100 g. Accordingly, in some embodiments, the oral formulation includes the L-ornithine phenyl acetate compositions disclosed herein in the range of about 500 mg to about 50 g. In some embodiments, the oral formulation is substantially free of alkali metal salts and halides (e.g., contains no more than trace amounts of alkali metal salts and halides).

Intravenous formulations may also generally include dosages of L-ornithine phenyl acetate in the range of about 500 mg to about 100 g (preferably about 1 g to about 50 g). In some embodiments, the intravenous formulation is substantially free of alkali metal salts and halides (e.g., contains no more than trace amounts of alkali metal salts and halides). In some embodiments, the intravenous formulation has a concentration of about 5 to about 300 mg/mL of L-ornithine phenyl acetate (preferably about 25 to about 200 mg/mL, and more preferably about 40 to about 60 mg/mL).

The composition, or medicament containing said composition, may optionally be placed is sealed packaging. The sealed packaging may reduce or prevent moisture and/or ambient air from contacting the composition or medicament. In some embodiments, the packaging includes a hermetic seal. In some embodiments, the packaging sealed under vacuum or with an inert gas (e.g., argon) within the sealed package. Accordingly, the packaging can inhibit or reduce the rate of degradation for the composition or medicament stored within the packaging. Various types of sealed packaging are known in the art. For example, U.S. Pat. No. 5,560,490, is hereby incorporate by reference in its entirety, discloses an exemplary sealed package for medicaments.

Crystalline Forms of L-Ornithine Phenyl Acetate

Also disclosed herein are crystalline forms of L-ornithine phenyl acetate, and in particular, crystalline Form I, Form II, Form III, and Form V. L-Ornithine phenyl acetate may, in some embodiments, be obtained using the processes disclosed above and then crystallized using any of the methods disclosed herein.

Form I

The precise conditions for forming crystalline Form I may be empirically determined and it is only possible to give a number of methods which have been found to be suitable in practice.

Thus, for example, crystalline Form I may generally be obtained by crystallizing L-ornithine phenyl acetate under controlled conditions. As an example, precipitating L-ornithine phenyl acetate from a saturated solution by adding ethanol at reduced temperatures (e.g., 4° or −21° C.). Exemplary solvents for the solution that yield crystalline Form I upon adding ethanol include, but are not limited to, cyclohexanone, 1-propanol, diemthylcarbonate, N-methylpyrrolidine (NMP), diethyl ether, 2-butanol, cumene, ethyl formate, isobutyl acetate, 3-methyl-1-butanol, and anisole.

Accordingly, in the context of the processes for making L-ornithine phenyl acetate disclosed above, the process can yield Form I by utilizing particular isolation methods. For example, L-ornithine phenyl acetate may be isolated by adding ethanol at reduced temperature to yield Form I.

Crystalline Form I was characterized using various techniques which are described in further detail in the experimental methods section. FIG. 1 shows the crystalline structure of Form I as determined by X-ray powder diffraction (XRPD). Form I, which may be obtained by the methods disclosed above, exhibits characteristic peaks at approximately 4.9°, 13.2°, 17.4°, 20.8° and 24.4° 2θ. Thus, in some embodiments, a crystalline form of L-ornithine phenyl acetate has one or more characteristic peaks (e.g., one, two, three, four or five characteristic peaks) selected from approximately 4.9°, 13.2°, 17.4°, 20.8°, and 24.4° 2θ.

As is well understood in the art, because of the experimental variability when X-ray diffraction patterns are measured on different instruments, the peak positions are assumed to be equal if the two theta (2θ) values agree to within 0.2° (i.e., ±0.2°). For example, the United States Pharmacopeia states that if the angular setting of the 10 strongest diffraction peaks agree to within ±0.2° with that of a reference material, and the relative intensities of the peaks do not vary by more than 20%, the identity is confirmed. Accordingly, peak positions within 0.2° of the positions recited herein are assumed to be identical.

Figure 2:
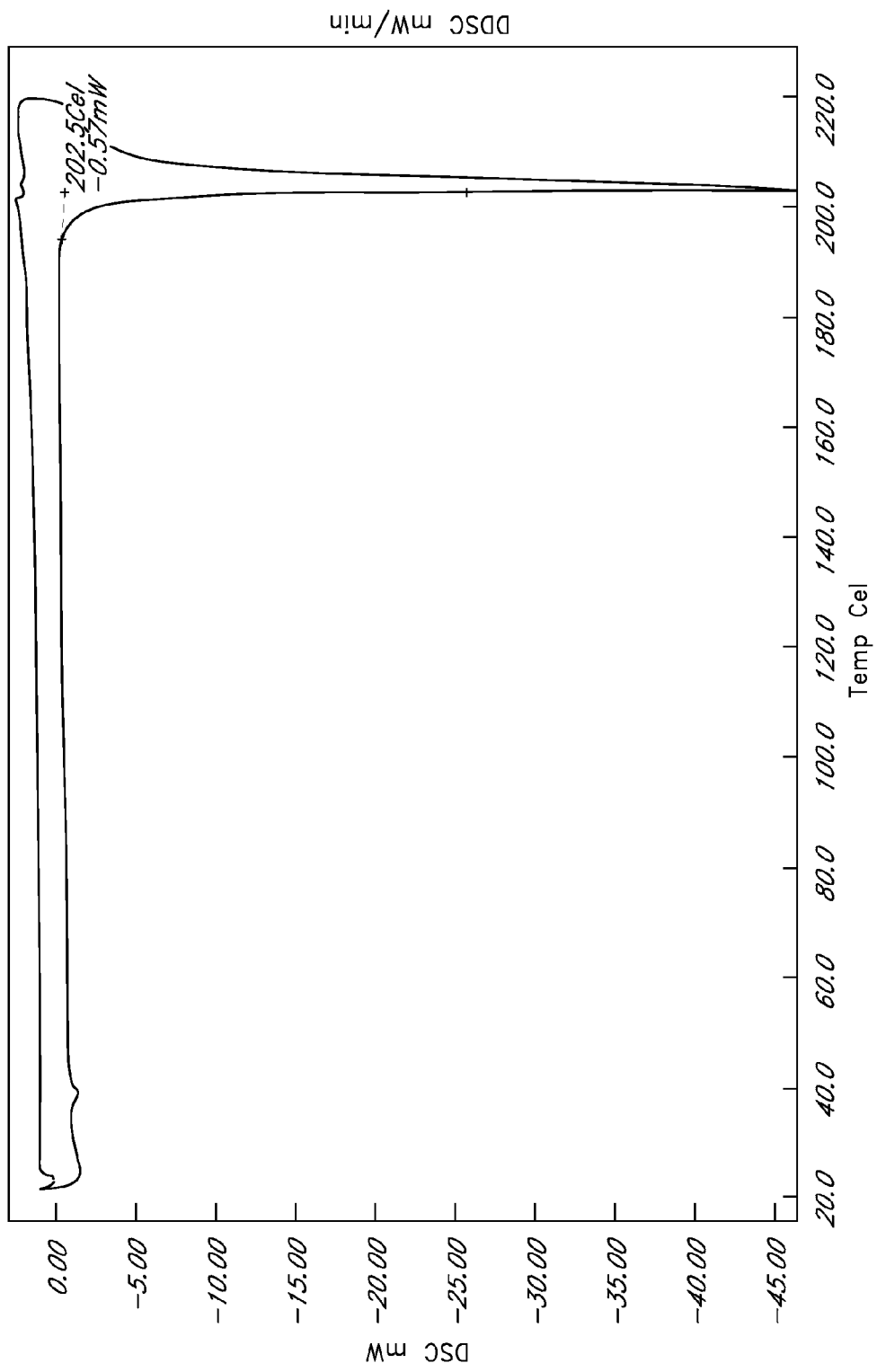
FIG. 2 shows differential scanning calorimetry results for Form I.
Figure 3:
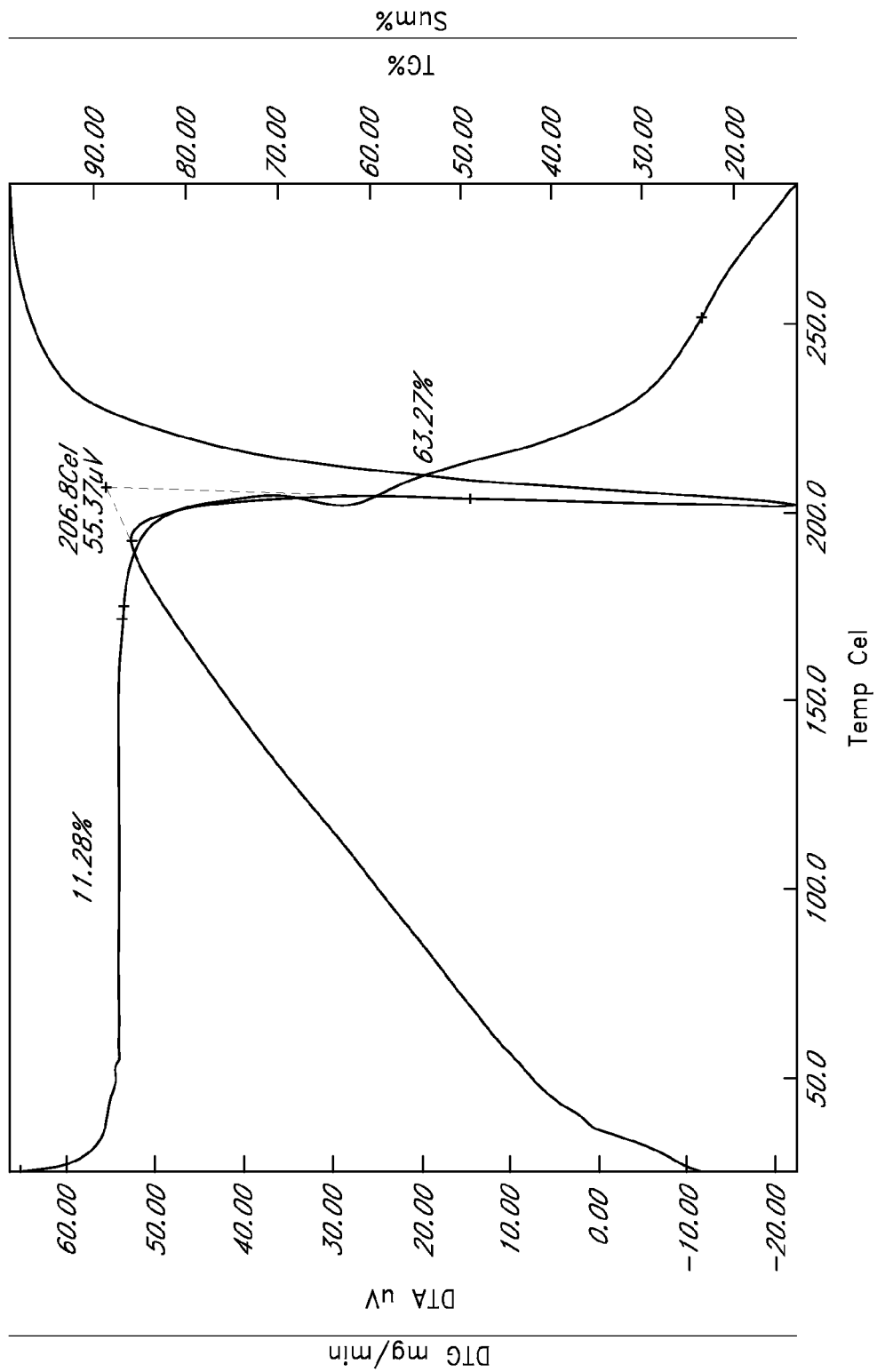
FIG. 3 shows thermogravimetric gravimetric/differential thermal analysis of Form I.

FIG. 2 shows results obtained by differential scanning calorimetry (DSC) for Form I. These results indicate an endotherm at 35° C., which is possibly associated with a desolvation and/or dehydration to Form II. A second transition at about 203° C. indicates the melting point for the crystal. To explore the possible existence of a desolvation and/or dehydration transition, Form I was analyzed by thermogravimetric gravimetric/differential thermal analysis (TG/DTA), which is shown in FIG. 3. Form I exhibits a 11.28% weight loss at about 35° C., and therefore these results further suggest that Form I exhibits a desolvation and/or dehydration transition at about 35° C. The melting point of about 203° C. could also be observed by TGA testing. Accordingly, in some embodiments, the crystalline form of L-ornithine phenyl acetate is characterized by differential scanning calorimetry as having an endotherm at about at about 35° C. In some embodiments, a crystalline form of L-ornithine phenyl acetate exhibits a weight loss of about 11% at about 35° C., as determined by TGA. In some embodiments, a crystalline form of L-ornithine phenyl acetate exhibits a melting point of about 203° C.

Figure 4:
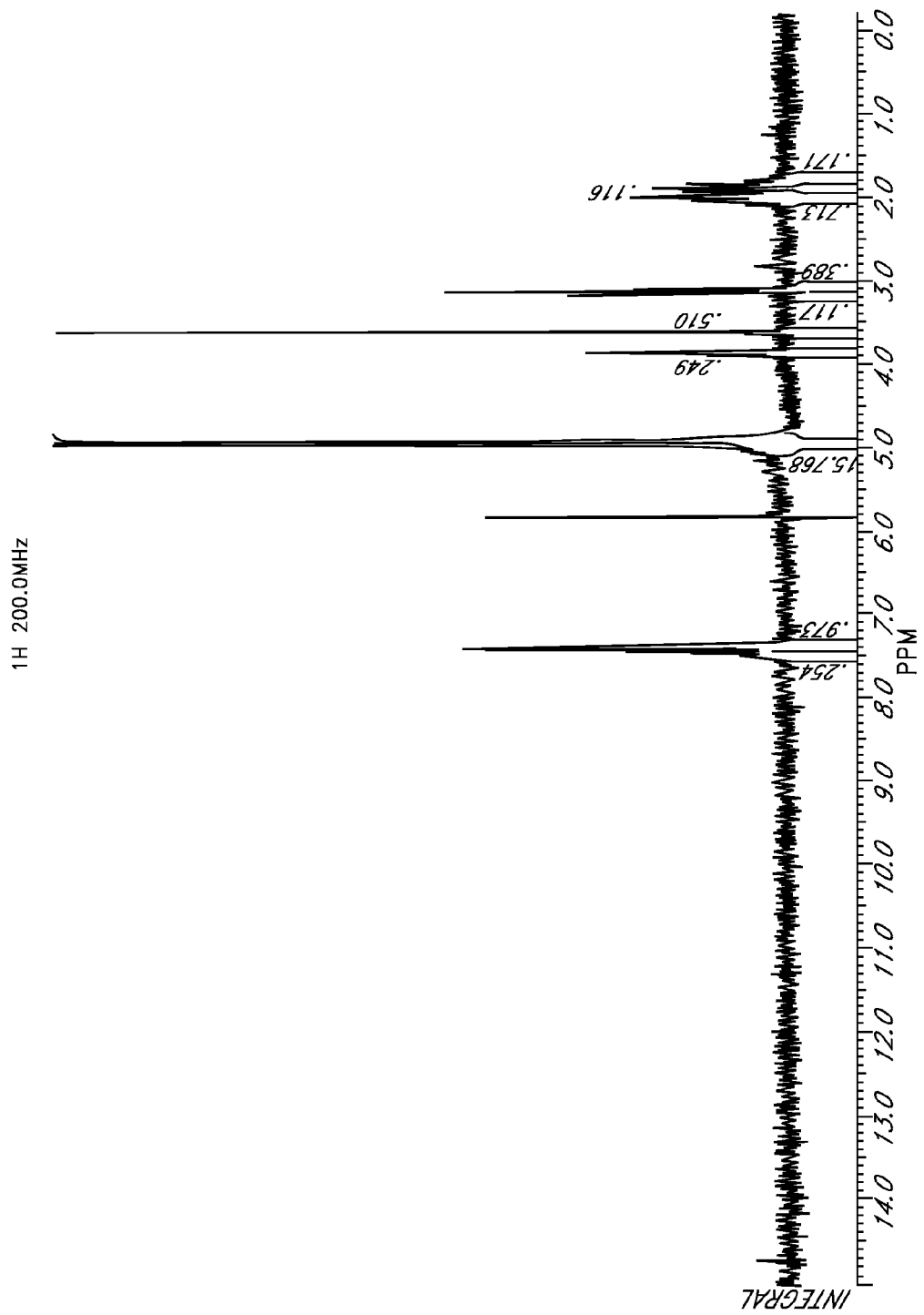
FIG. 4 shows the $^1$H nuclear magnetic resonance spectrum obtained from a sample of Form I.
Figure 5:
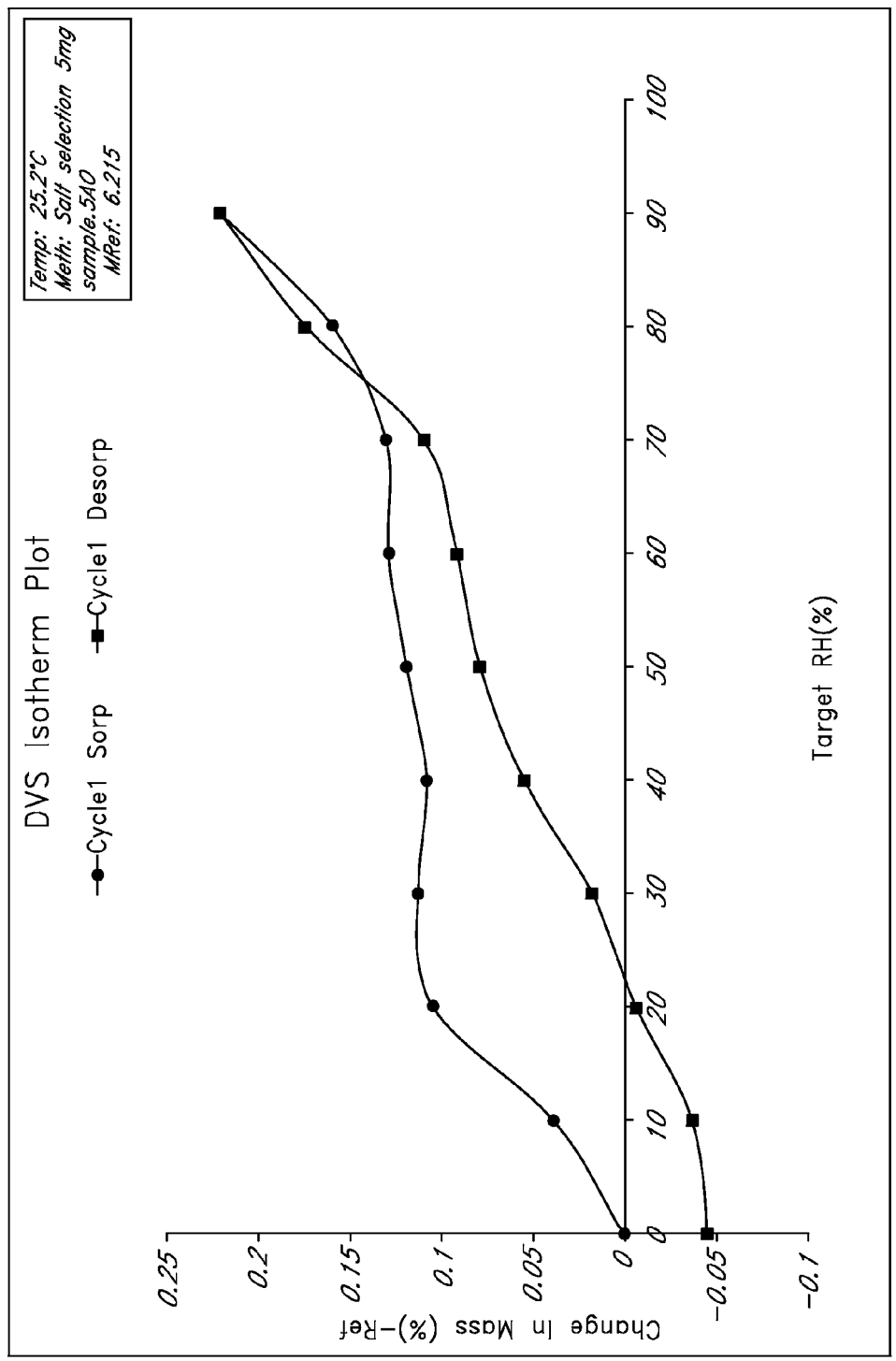
FIG. 5 shows dynamic vapor sorption results for Form I.

FIG. 4 shows nuclear magnetic resonance (NMR) integrals and chemical shifts for Form I. The integrals confirm the presence of L-ornithine phenyl acetate: 7.5 (aromatic CH), 3.8 (CH adjacent to $NH_2$), 3.6 ($CH_2$ unit of phenyl acetate), 3.15 ($CH_2$ adjacent to $NH_2$) and 1.9 (aliphatic $CH_2$ units) ppm (integrals: 5:1:2:2:4 protons; 1.2, 0.25, 0.5, 0.5, 1.0). Amine protons and hydroxylprotons were not observed due to proton exchange at both the zwitterion and site of salt formation. Meanwhile, FIG. 5 shows dynamic vapor sorption (DVS) results for Form I, and show a water uptake of about 0.2% by weight. XRPD results following DVA analysis (not shown) confirm that Form I did not transition to a different polymorph. Form I can therefore be characterized as non-hygroscopic and stable over a wide range of humidity.

A 7-day stability study of Form I at 40° C./75% RH indicated that a transformation to Form II occurred under these conditions. Form I also converts to Form II at elevated temperatures (e.g., 80° or 120° C.), with or without applying a vacuum, after 7 or 14 days. Accordingly, Form I is metastable.

Single crystal x-ray diffraction (SXRD) was also used to determine the structure of Form I at −20° and −123° C., and the results are summarized in TABLES 1 and 2. The results confirm that Form I is a solvate having ethanol and water molecules within the unit cell. In some embodiments, a crystalline form of L-ornithine phenyl acetate can be represented by the formula $C_{15}H_{28}N_2O_6$. In some embodiments, a crystalline form of L-ornithine phenyl acetate can be represented by the formula $[C_5H_{13}N_2O_2][C_8H_7O_2]EtOH.H_2O$. In some embodiments, a crystalline form of L-ornithine phenyl acetate exhibits a single crystal X-ray crystallographic analysis with crystal parameters approximately equal to the following: unit cell dimensions of a=5.3652(4) Å, b=7.7136(6)

Å, c=20.9602(18) Å, α=90°, β=94.986(6)°, γ=90°; a monoclinic crystal system, and a P2$_1$ space group.

TABLE 1

Crystallographic Data of Form I Collected at −20° C.

| | |
|---|---|
| Empirical Formula | C$_{15}$H$_{28}$N$_2$O$_6$ or [C$_5$H$_{13}$N$_2$O$_2$][C$_8$H$_7$O$_2$]EtOH•H$_2$O |
| Formula Weight | 332.39 |
| Crystal System | Monoclinic |
| Space Group | P2$_1$ |
| Unit Cell Dimensions | a = 5.3652(4) Å α = 90° |
| | b = 7.7136(6) Å β = 94.986(6)° |
| | c = 20.9602(18) Å γ = 90° |
| Volume | 864.16(12) Å$^3$ |
| Number of Reflections | 1516 (2.5° < θ < 28°) |
| Density (calculated) | 1.277 mg/cm$^3$ |

TABLE 2

Crystallographic Data of Form I Collected at −123° C.

| | |
|---|---|
| Empirical Formula | C$_{15}$H$_{28}$N$_2$O$_6$ or [C$_5$H$_{13}$N$_2$O$_2$][C$_8$H$_7$O$_2$]EtOH•H$_2$O |
| Formula Weight | 332.39 |
| Crystal System | Monoclinic |
| Space Group | P2$_1$ |
| Unit Cell Dimensions | a = 5.3840(9) Å α = 90° |
| | b = 7.7460(12) Å β = 95.050(12)° |
| | c = 21.104(4) Å γ = 90° |
| Volume | 876.7(3) Å$^3$ |
| Number of Reflections | 1477 (2.5° < θ < 18°) |
| Density (calculated) | 1.259 mg/cm$^3$ |

Form II

The precise conditions for forming crystalline Form II may be empirically determined and it is only possible to give a number of methods which have been found to be suitable in practice.

Thus, for example, crystalline Form II may be prepared by crystallization under controlled conditions. Crystalline Form II can be prepared by, for example, evaporating a saturated organic solution of L-ornithine phenyl acetate. Non-limiting examples of organic solutions that may be used to obtain Form II include ethanol, acetone, benzonitrile, dichloromethane (DCM), dimethyl sulfoxide (DMSO), ethyl acetate (EtOAc), acetonitrile (MeCN), methyl acetate (MeOAc), nitromethane, tert-butyl methyl ether (TBME), tetrahydrofuran, and toluene. Other solvents may yield a mixture of Form I and II, such as, but not limited to, 1,4 dioxane, 1-butanol, cyclohexane, IPA, THF, MEK, MeOAc and water.

Form II can also be obtained by precipitating L-ornithine phenyl acetate from a saturated organic solution by adding an anti-solvent for L-ornithine phenyl acetate, such as IPA. Form II may be precipitated over a broad range of temperatures (e.g., room temperature, 4° C., and −21° C.). Non-limiting examples of suitable solvents for the saturated organic solution include cyclohexanone, 1-propanol, dimethyl carbonate, N-methylpyrrolidone (NMP), diisopropyl ether, diethyl ether, ethylene glycol, dimethylformamide (DMF), 2-butanol, cumene, isobutyl acetate, 3-methyl-1-butanol, and anisole. Alternatively, the same listed solvents (e.g., cyclohexanone) can be used to form a solution of L-ornithine phenyl acetate, and Form II may be precipitated by adding ethanol at ambient conditions. As another example, Form II may also be obtained by forming a slurry of L-ornithine phenyl acetate with the listed organic solvents and cycling the temperature between 25° and 40° C. every 4 hours for about 18 cycles (or 72 hours).

Accordingly, in the context of the processes for making L-ornithine phenyl acetate disclosed above, the process can yield Form II by utilizing particular isolation methods. For example, L-ornithine phenyl acetate may by isolated by adding IPA, or evaporating the organic solvent, to yield Form II.

Figure 6:
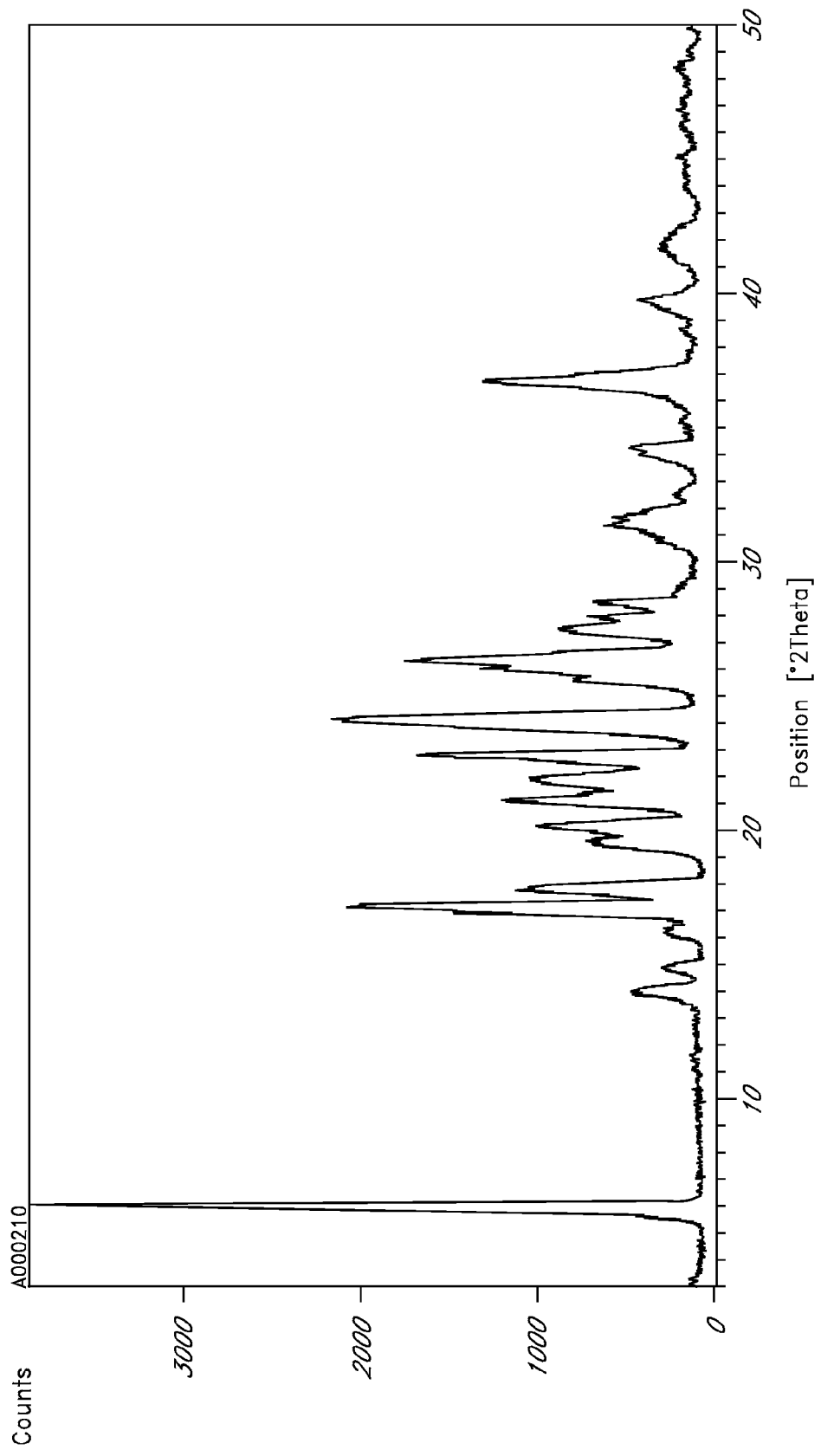
FIG. 6 is an X-ray powder diffraction pattern of Form II.

FIG. 6 shows the crystalline structure of Form II as determined by XRPD. Form II, which may be obtained by the methods disclosed above, exhibits characteristic peaks at approximately 6.0°, 13.9°, 14.8°, 17.1°, 17.8° and 24.1° 2θ. Thus, in some embodiments, a crystalline form of L-ornithine phenyl acetate has one or more characteristic peaks (e.g., one, two, three, four, five or six characteristic peaks) selected from approximately 6.0°, 13.9°, 14.8°, 17.1°, 17.8° and 24.12° θ.

Figure 7:
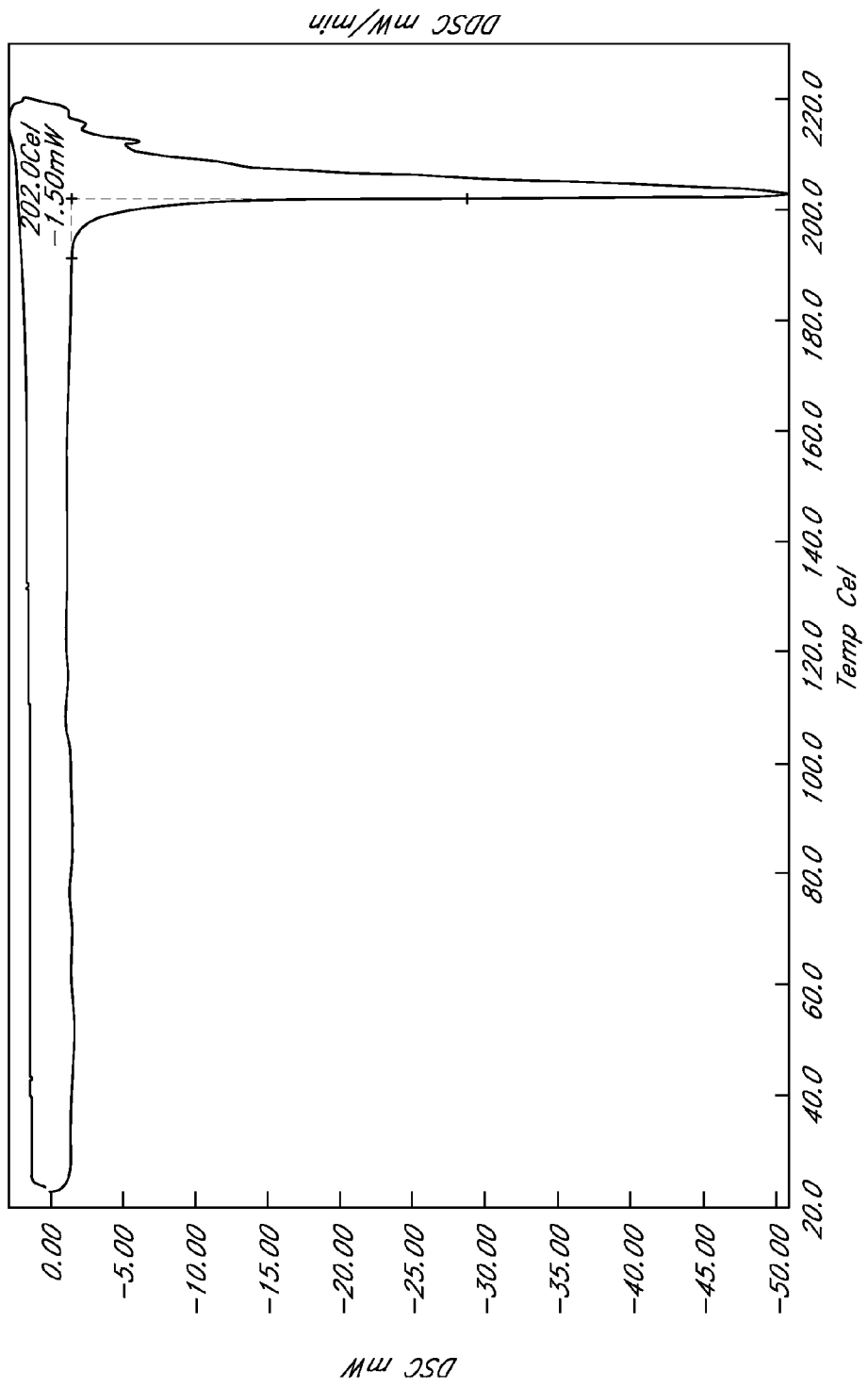
FIG. 7 shows differential scanning calorimetry results for Form II.
Figure 8:
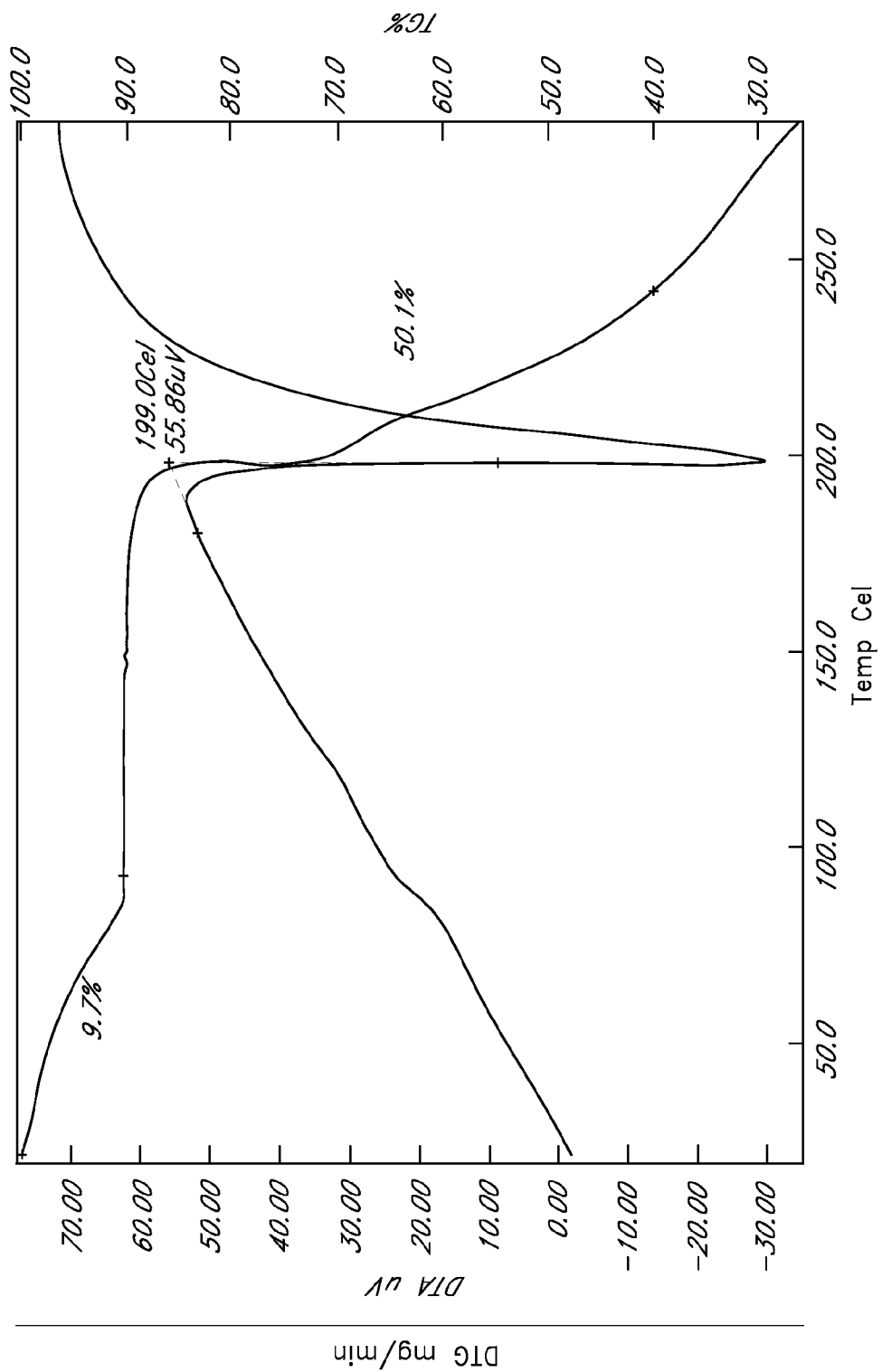
FIG. 8 shows thermogravimetric gravimetric/differential thermal analysis of Form II.

FIG. 7 shows results obtained by differential scanning calorimetry (DSC) for Form II. These results indicate a melting point of about 202° C., which is approximately the same as the melting point for Form I. This suggests that Form I transitions to Form II upon heating above about 35° C. Form II was also analyzed using TG/DTA, as shown in FIG. 8, and exhibits an about 9.7% weight loss associated with residual solvent. The melting point of about 202° C. could also be observed by TGA testing. Accordingly, in some embodiments, a crystalline form of L-ornithine phenyl acetate exhibits a melting point of about 202° C.

A 7-day stability study of Form II at 40° C./75% RH failed to produce an observable phase change. In fact, Form II was stable over 14 days when exposed to elevated temperatures, varying pHs, UV light or oxygen. Accordingly, Form II is considered stable.

Figure 9:
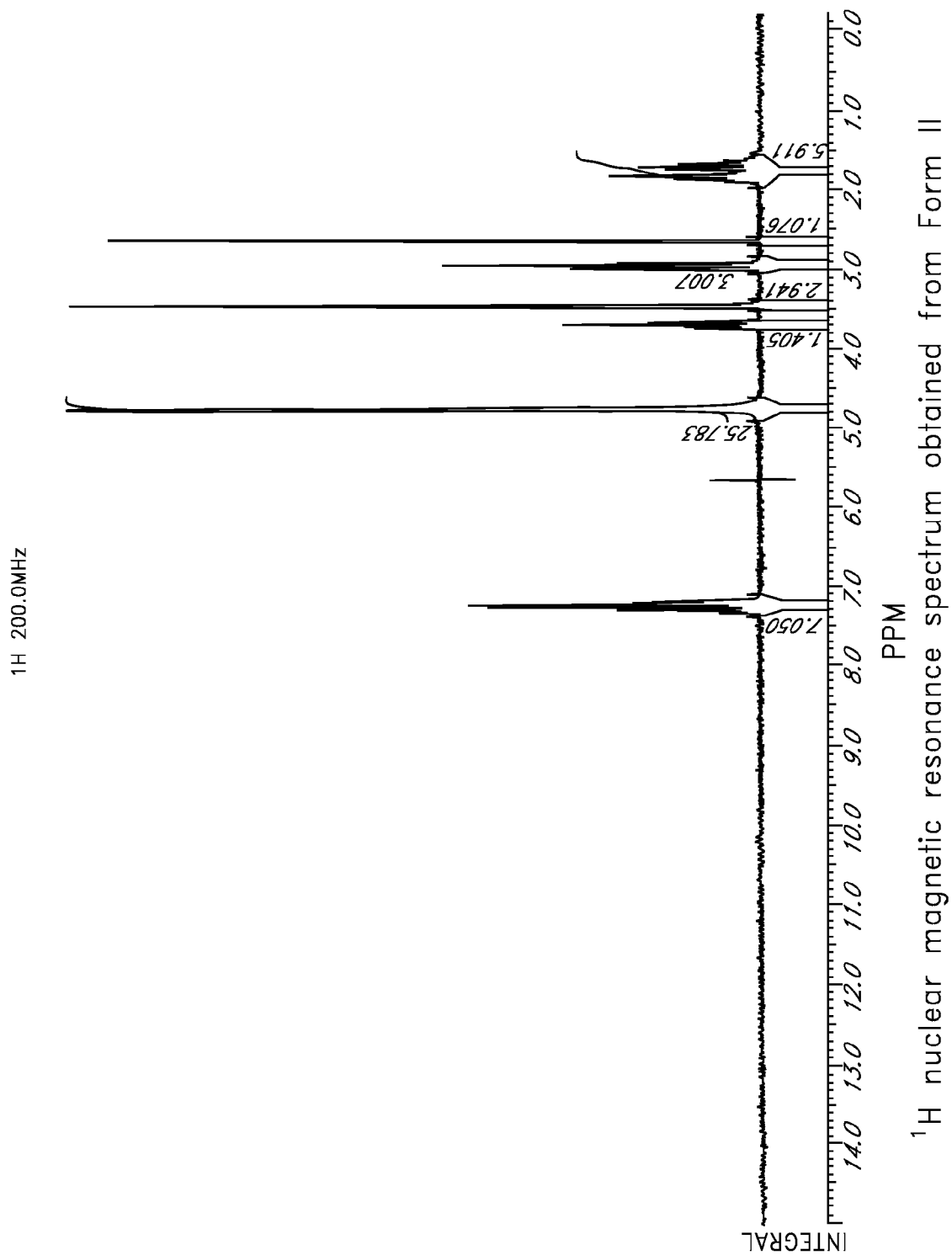
FIG. 9 shows the $^1$H nuclear magnetic resonance spectrum obtained from a sample of Form II.
Figure 10:
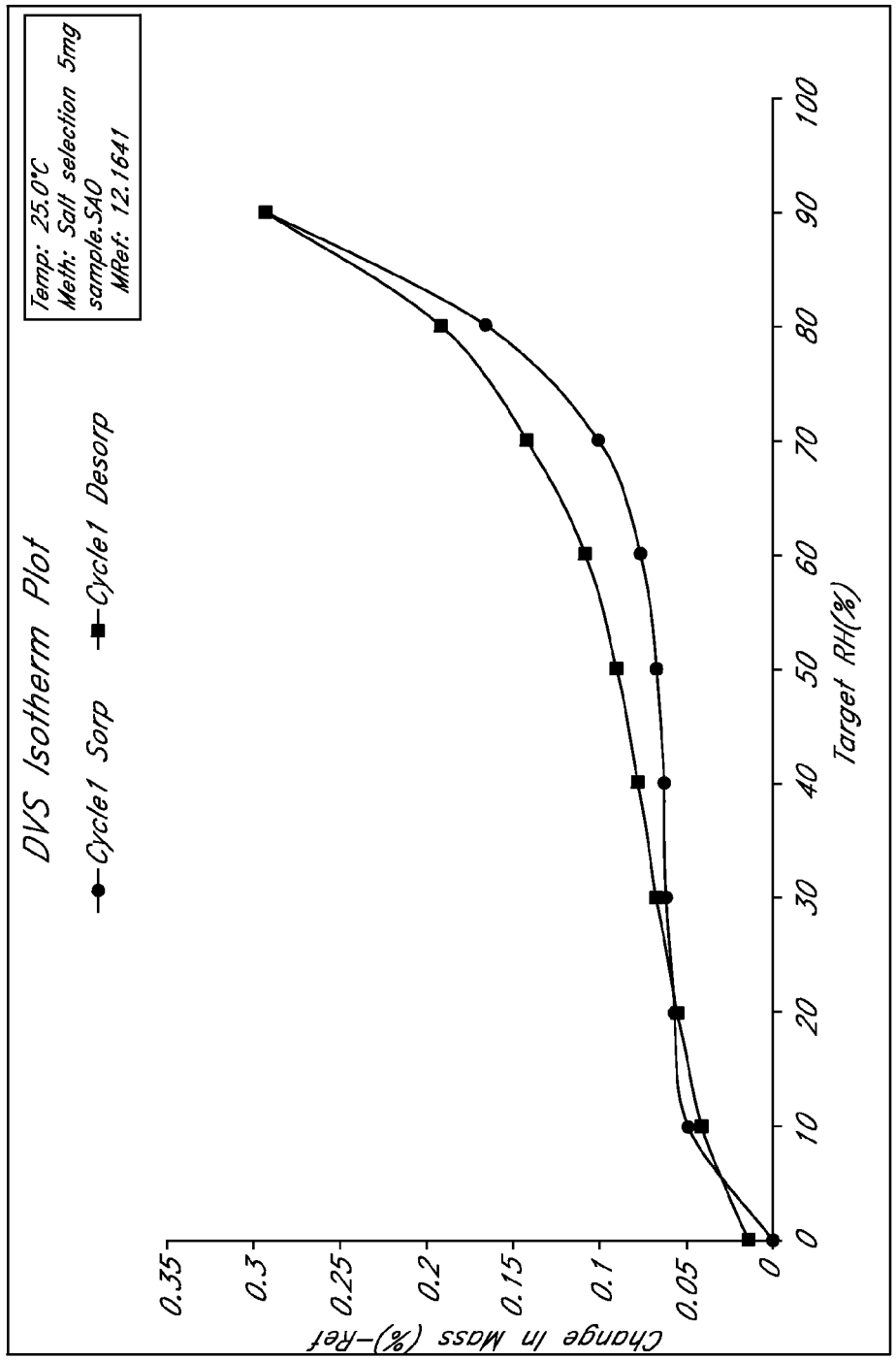
FIG. 10 shows dynamic vapor sorption results for Form II.

FIG. 9 shows nuclear magnetic resonance (NMR) integrals and chemical shifts for Form II. The integrals confirm the presence of L-ornithine phenyl acetate: 7.5 (aromatic CH), 3.8 (CH adjacent to NH2), 3.6 (CH2 unit of phenylacetate), 3.15 (CH2 adjacent to NH2) and 1.9 (aliphatic CH2 units) ppm (integrals: 5:1:2:2:4 protons; 7.0, 1.4, 2.9, 3.0, 5.9). Amine protons and hydroxylprotons were not observed due to proton exchange at both the zwitterion and site of salt formation. Meanwhile, FIG. 10 shows dynamic vapor sorption (DVS) results for Form II, and show a water uptake of about 0.3% by weight. XRPD results following DVA analysis (not shown) confirm that Form II did not transition to a different polymorph. Form II can therefore be characterized as non-hygroscopic and stable over a wide range of humidity.

Single crystal x-ray diffraction (SXRD) was also used to determine the structure of Form II at 23° and −123° C., and the results are summarized in TABLES 3 and 4. The results demonstrate that Form II is anhydrous and therefore structurally different from Form I. In some embodiments, a crystalline form of L-ornithine phenyl acetate can be represented by the formula C$_{13}$H$_{20}$N$_2$O$_4$. In some embodiments, a crystalline form of L-ornithine phenyl acetate can be represented by the formula [C$_5$H$_{13}$N$_2$O$_2$][C$_8$H$_7$O$_2$]. In some embodiments, a crystalline form of L-ornithine phenyl acetate exhibits a single crystal X-ray crystallographic analysis with crystal parameters approximately equal to the following: unit cell dimensions of a=6.594(2) Å, α=90°, b=6.5448(18) Å, β=91.12(3)°, c=31.632(8) Å, γ=90°; a monoclinic crystal system; and a P2$_1$ space group.

TABLE 3

Crystallographic Data of Form II Collected at 23° C.

| | |
|---|---|
| Empirical Formula | C$_{13}$H$_{20}$N$_2$O$_4$ or [C$_5$H$_{13}$N$_2$O$_2$][C$_8$H$_7$O$_2$] |
| Formula Weight | 268.31 |
| Crystal System | Monoclinic |
| Space Group | P2$_1$ |

TABLE 3-continued

Crystallographic Data of Form II Collected at 23° C.

| | |
|---|---|
| Unit Cell Dimensions | a = 6.594(2) Å α = 90° |
| | b = 6.5448(18) Å β = 91.12(3)° |
| | c = 31.632(8) Å γ = 90° |
| Volume | 1364.9(7) Å$^3$ |
| Number of Reflections | 3890 (3° < θ < 20.5°) |
| Density (calculated) | 1.306 mg/cm$^3$ |

TABLE 4

Crystallographic Data of Form II Collected at −123° C.

| | |
|---|---|
| Empirical Formula | $C_{15}H_{28}N_2O_6$ or $[C_5H_{13}N_2O_2][C_8H_7O_2]$ |
| Formula Weight | 332.39 |
| Crystal System | Monoclinic |
| Space Group | P2$_1$ |
| Unit Cell Dimensions | a = 5.3652(4) Å α = 90° |
| | b = 7.7136(6) Å β = 94.986(6)° |
| | c = 20.9602(18) Å γ = 90° |
| Volume | 864.16(12) Å$^3$ |
| Number of Reflections | 1516 (2.5° < θ < 28°) |
| Density (calculated) | 1.277 mg/cm$^3$ |

Form III

The precise conditions for forming crystalline Form III may be empirically determined and it is only possible to give a number of methods which have been found to be suitable in practice.

Thus, for example, Form III may be obtained by placing a saturated solution of L-ornithine phenyl acetate in a cooled temperature environment of about −21° C., where the solution is a mixture of acetone and water (e.g., equal parts volume of acetone and water). As another example, adding IPA to a saturated solution of L-ornithine phenyl acetate in 2-butanol can yield Form III when completed at ambient conditions. Furthermore, Form III may be obtained, for example, by adding IPA to a saturated solution of L-ornithine phenyl acetate in isobutyl acetate when completed at reduced temperatures of about −21° C.

Accordingly, in the context of the processes for making L-ornithine phenyl acetate disclosed above, the process can yield Form III by utilizing particular solvents and isolation methods. For example, L-ornithine phenyl acetate may be formed within a mixture of acetone and water, and subsequently placed in a cool environment of about −21° C. to yield Form III.

Figure 11:
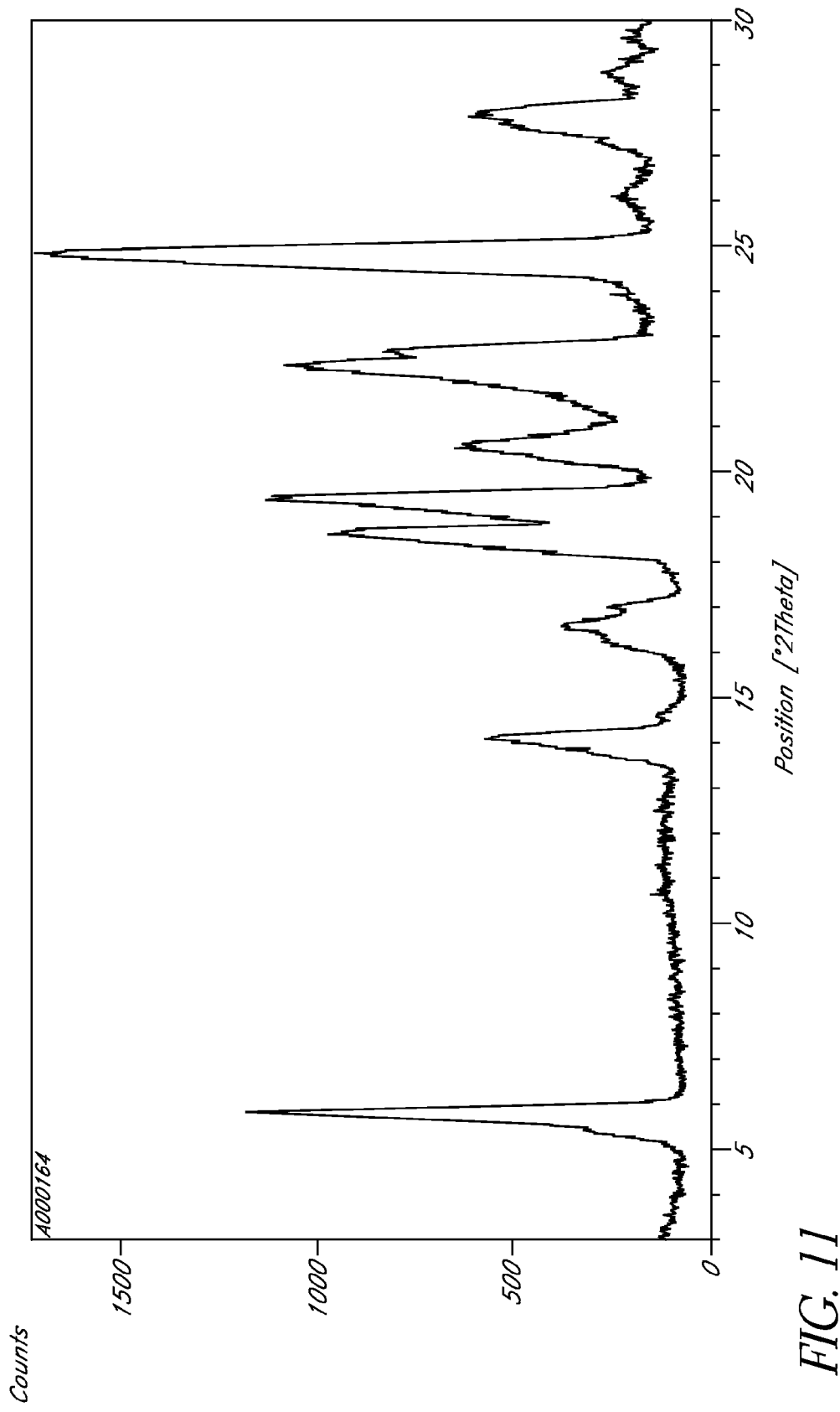
FIG. 11 is an X-ray powder diffraction pattern of Form III.

FIG. 11 shows the crystalline structure of Form III as determined by XRPD. Form III, which may be obtained by the methods disclosed above, exhibits characteristic peaks at approximately 5.8°, 14.1°, 18.6°, 19.4°, 22.3° and 24.8° 2θ. Thus, in some embodiments, a crystalline form of L-ornithine phenyl acetate has one or more characteristic peaks (e.g., one, two, three, four, five or six characteristic peaks) selected from approximately 5.8°, 14.1°, 18.6°, 19.4°, 22.3° and 24.8° 2θ.

Figure 12:
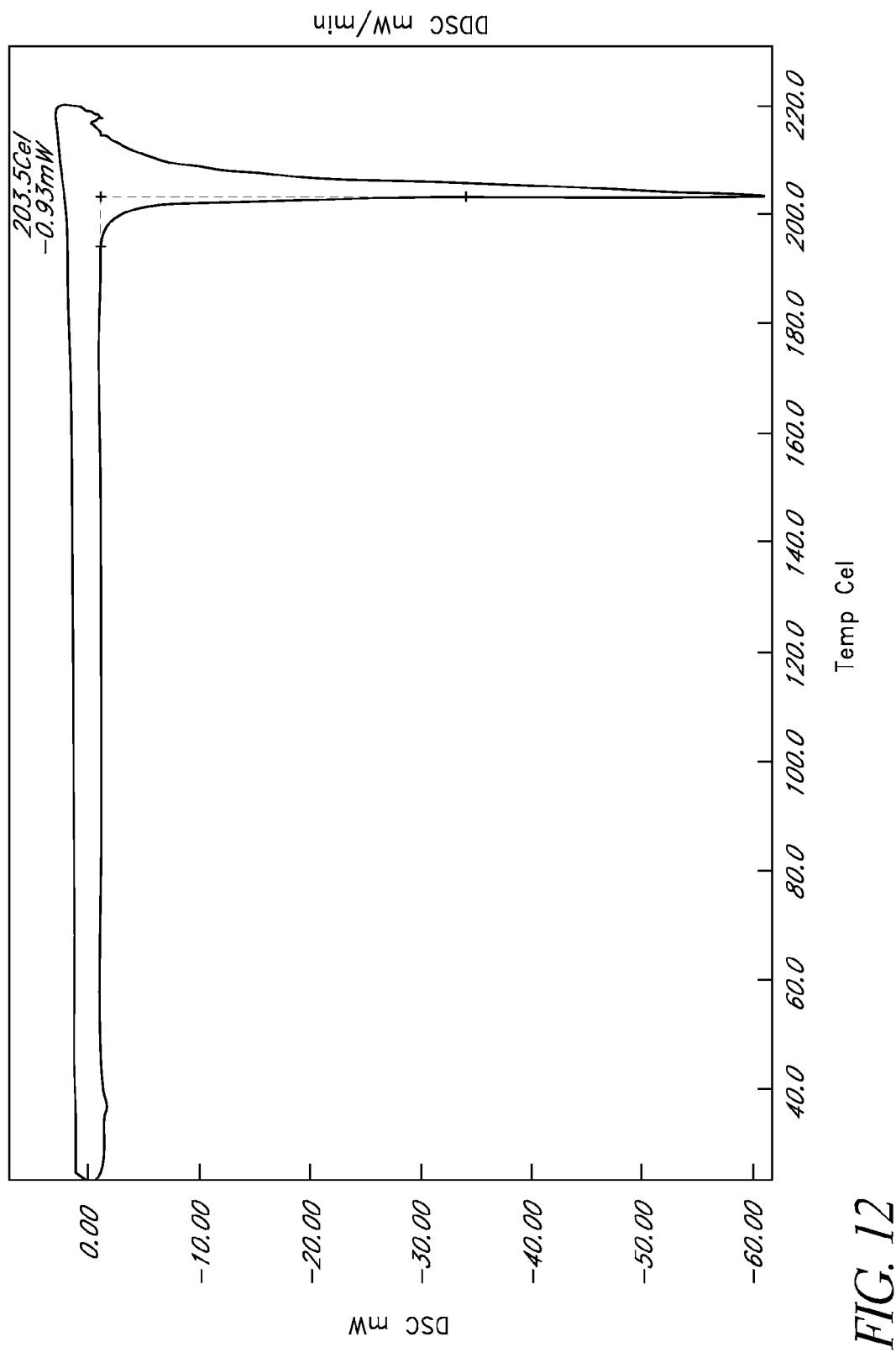
FIG. 12 shows differential scanning calorimetry results for Form III.
Figure 13:
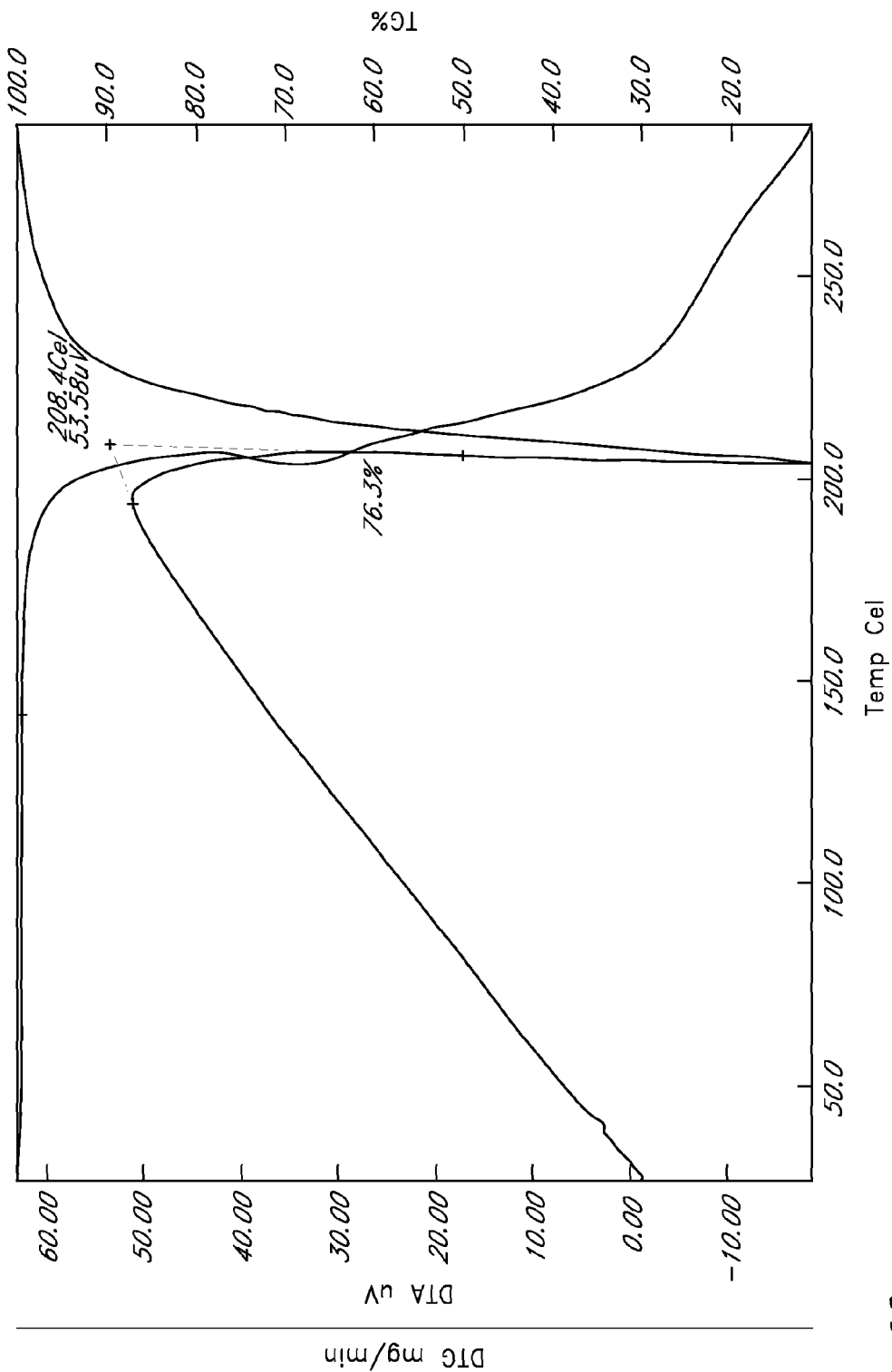
FIG. 13 shows thermogravimetric gravimetric/differential thermal analysis of Form III.

FIG. 12 shows results obtained by differential scanning calorimetry (DSC) for Form III. These results indicate a melting point of about 203° C., which is approximately the same as the melting points for Form I and Form II. Additionally, Form III exhibits an endotherm at about 40° C. Form III was also analyzed using TG/DTA, as shown in FIG. 13, and exhibits no significant weight loss before the melting point. Form III may therefore be characterized as anhydrous. The melting point of about 203° C. could also be observed by TGA testing. Accordingly, in some embodiments, a crystalline form of L-ornithine phenyl acetate exhibits a melting point of about 203° C. In some embodiments, a crystalline form of L-ornithine phenyl acetate is characterized by differential scanning calorimetry as having an endotherm at about 40° C. In some embodiments, a crystalline form of L-ornithine phenyl acetate is anhydrous.

A 7-day stability study of Form III at 40° C./75% RH indicated that a transformation to Form II occurred under these conditions. In contrast, Form II is stable at elevated temperatures, with or without vacuum, for periods of 7 or 10 days. Accordingly, Form III is most likely metastable, but more stable than Form I.

Figure 14:
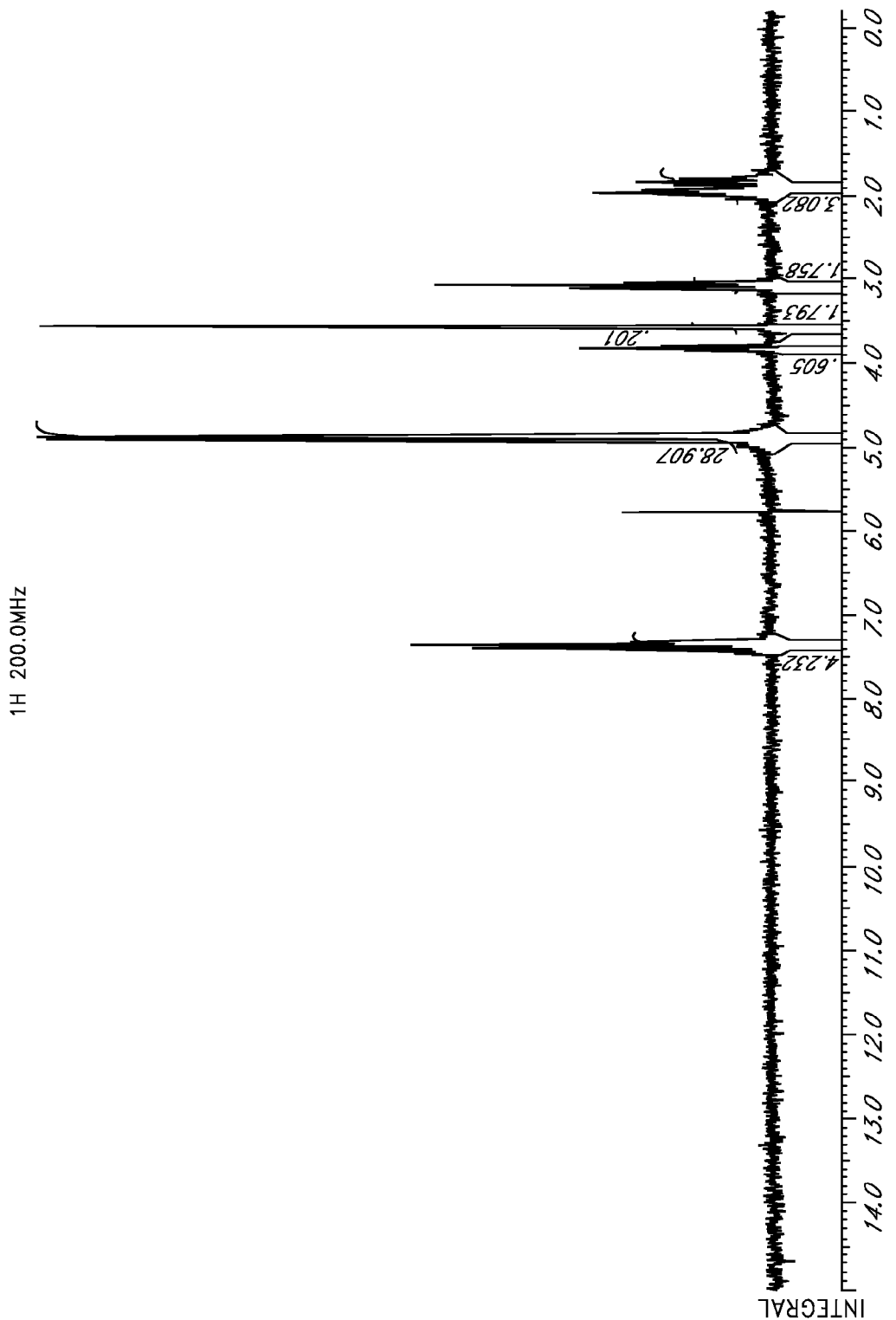
FIG. 14 shows the $^1$H nuclear magnetic resonance spectrum obtained from a sample of Form III.
Figure 15:
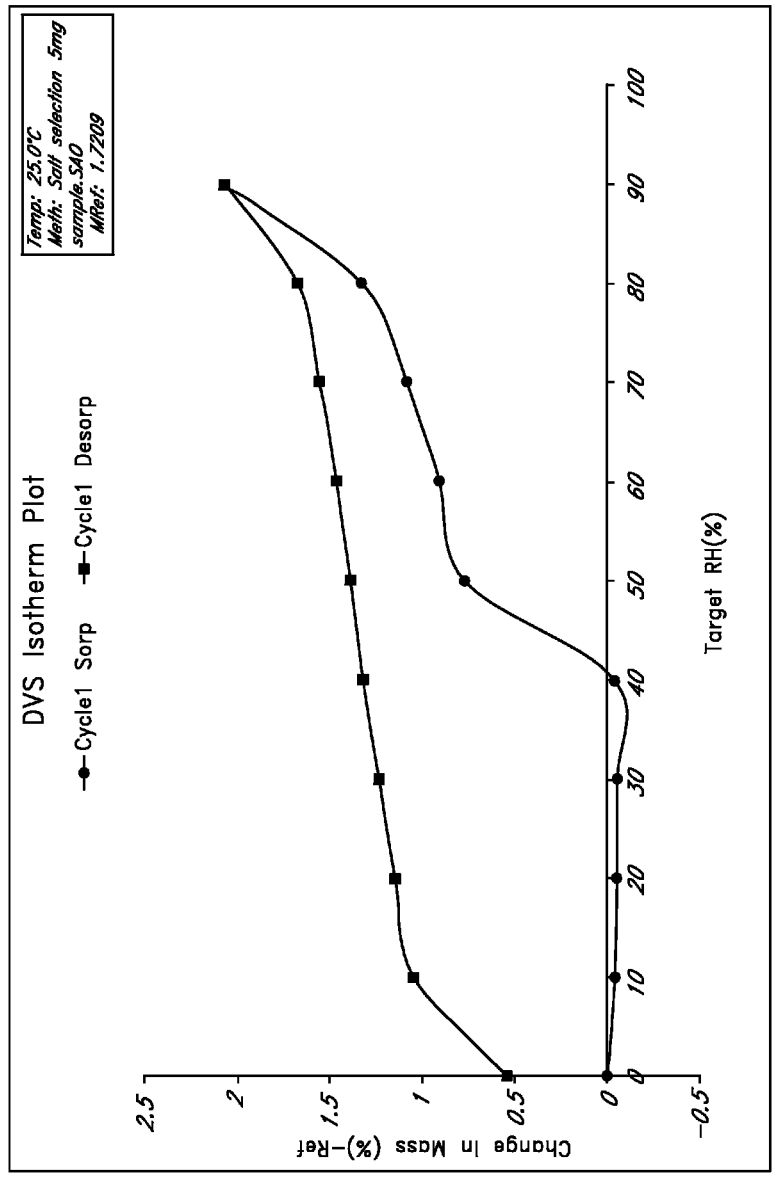
FIG. 15 shows dynamic vapor sorption results for Form III.

FIG. 14 shows nuclear magnetic resonance (NMR) integrals and chemical shifts for Form III. The integrals confirm the presence of L-ornithine phenyl acetate: 7.5 (aromatic CH), 3.8 (CH adjacent to NH2), 3.6 (CH2 unit of phenyl acetate), 3.15 (CH2 adjacent to NH2) and 1.9 (aliphatic CH2 units) ppm (integrals: 5:1:2:2:4 protons; 4.2, 0.8, 1.7, 1.7, 3.0). Amine protons and hydroxylprotons were not observed due to proton exchange at both the zwitterion and site of salt formation. Meanwhile, FIG. 15 shows dynamic vapor sorption (DVS) results for Form III, and show a water uptake of about 2.0% by weight. XRPD results following DVS analysis (not shown) confirm that Form III did not transition to a different polymorph. Form III therefore exhibits greater water uptake compared to Forms I and II; however Form III is still characterized as non-hygroscopic and stable over a wide range of humidity at room temperature.

Form V

The precise conditions for forming crystalline Form V may be empirically determined and it is only possible to give a number of methods which have been found to be suitable in practice.

Thus, for example, Form V may be obtained by placing a saturated solution of L-ornithine phenyl acetate in a cooled temperature environment of about −21° C., where the solution is cyclohexanone. As another example, the same saturated solution may yield Form V when evaporating the solvent.

Form V also forms from saturated solutions of L-ornithine phenyl acetate having diisopropyl ether as a solvent. For example, a saturated solution having a solvent ratio of about 1 to 2 of diisopropyl ether and IPA will yield Form V when placed in a cooled temperature environment of about 4° C. Similarly, a solution having only the solvent diisopropyl ether can yield Form V when placed in a cooled temperature environment of about −21° C.

Figure 16:
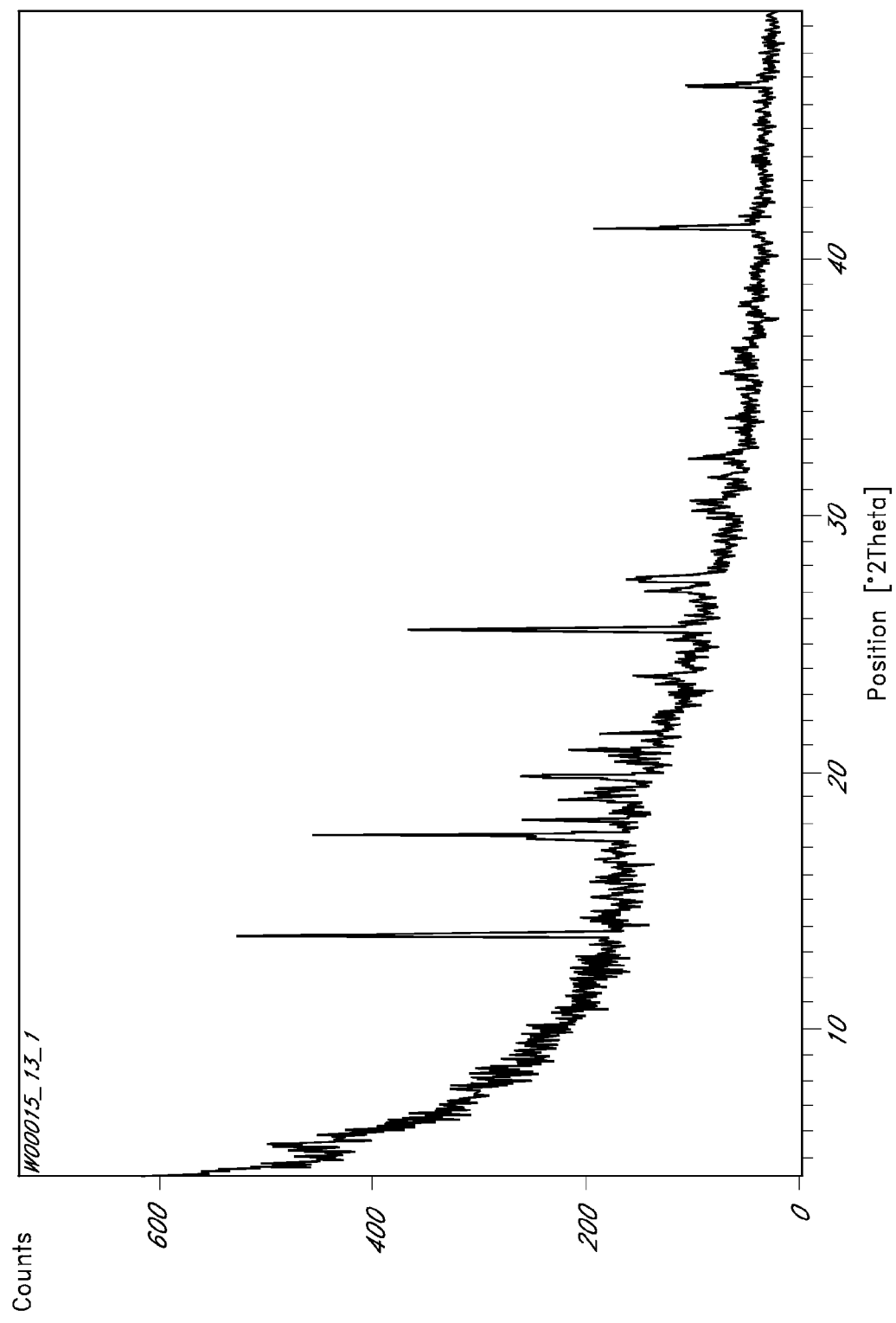
FIG. 16 is an X-ray powder diffraction pattern of Form V.

FIG. 16 shows the crystalline structure of Form V as determined by XRPD. Form V, which may be obtained by the methods disclosed above, exhibits characteristic peaks at approximately 13.7°, 17.4°, 19.8°, 20.6° and 23.7° 2θ. Thus, in some embodiments, a crystalline form of L-ornithine phenyl acetate has one or more characteristic peaks (e.g., one, two, three, four, or five characteristic peaks) selected from approximately 13.7°, 17.4°, 19.8°, 20.6° and 23.7° 2θ.

Figure 17:
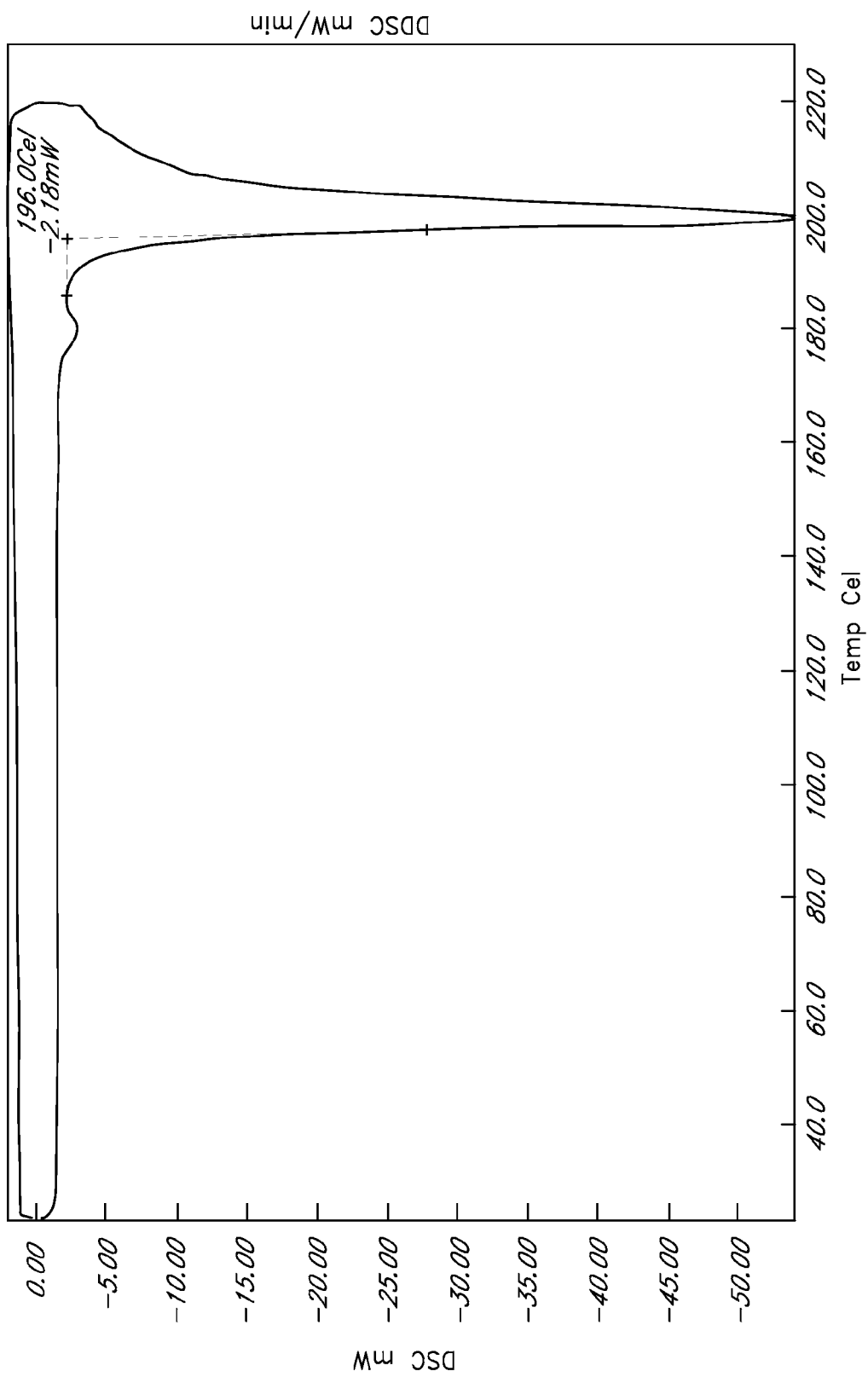
FIG. 17 shows differential scanning calorimetry results for Form V.
Figure 18:
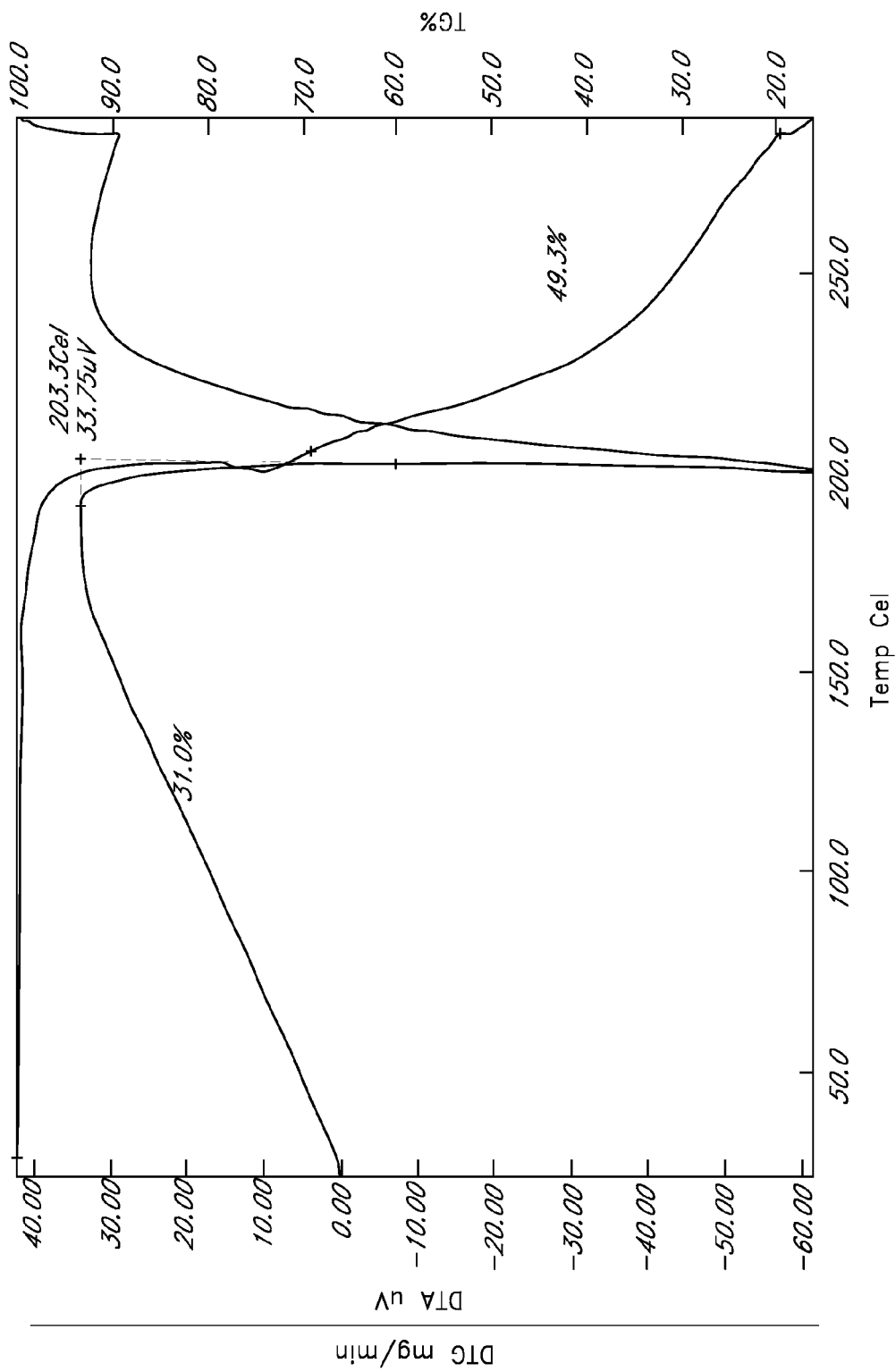
FIG. 18 shows thermogravimetric gravimetric/differential thermal analysis of Form V.

FIG. 17 shows results obtained by differential scanning calorimetry (DSC) for Form V. These results indicate a melting point of about 196° C., which is below the melting point of other forms. Form V also exhibits an endotherm at about 174° C. Form V was also analyzed using thermal gravimetric analysis (TGA), as shown in FIG. 18, and exhibits no significant weight loss before the melting point. Form V may therefore be characterized as anhydrous. The melting point of about 196° C. could also be observed by TGA testing. Accordingly, in some embodiments, a crystalline form of L-ornithine phenyl acetate exhibits a melting point of about 196° C. In some embodiments, a crystalline form of L-ornithine phenyl acetate is characterized by differential scanning calorimetry as having an endotherm at about 174° C. In some embodiments, a crystalline form of L-ornithine phenyl acetate is anhydrous.

Figure 19:
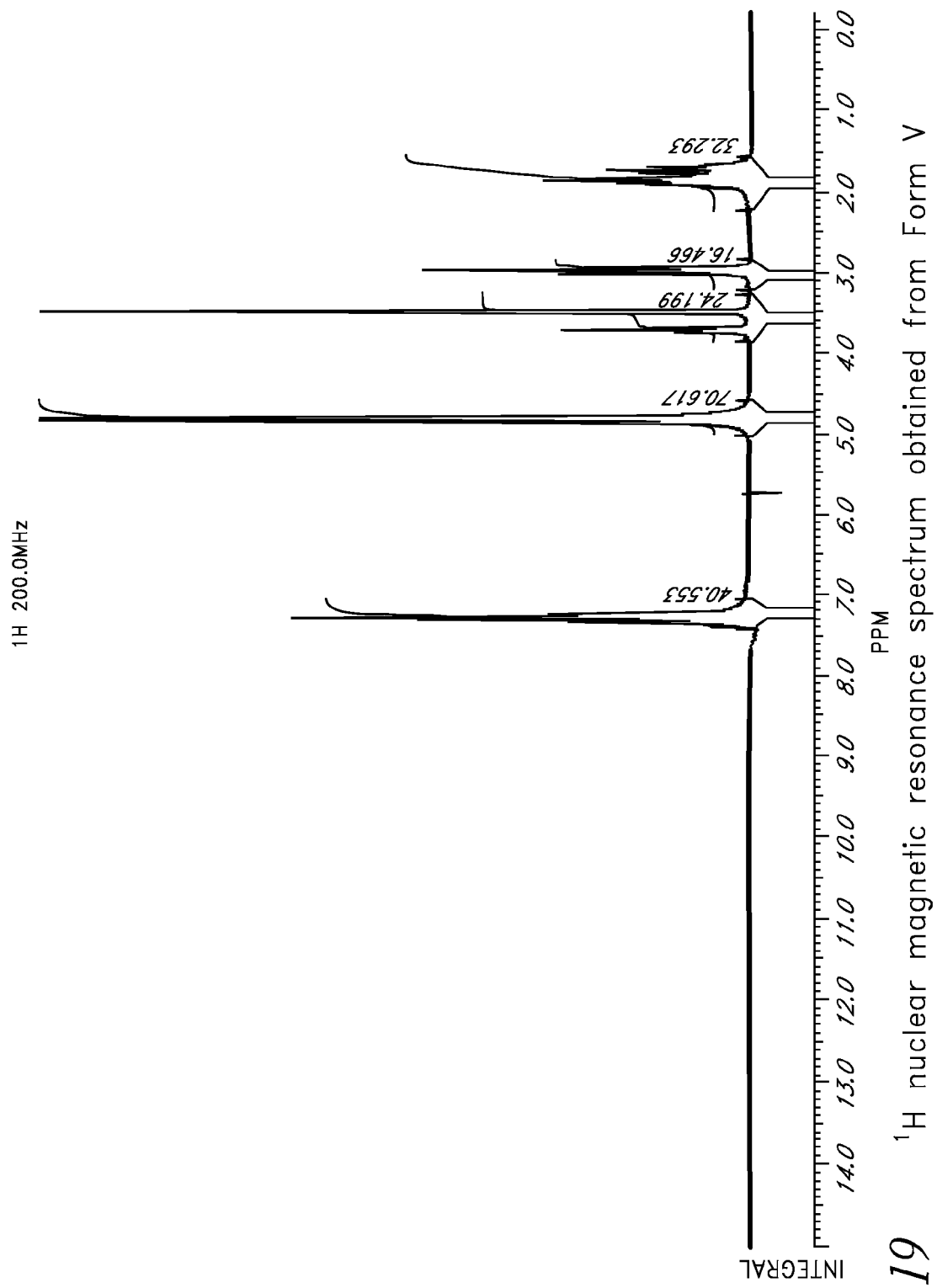
FIG. 19 shows the $^1$H nuclear magnetic resonance spectrum obtained from a sample of Form V.
Figure 20:
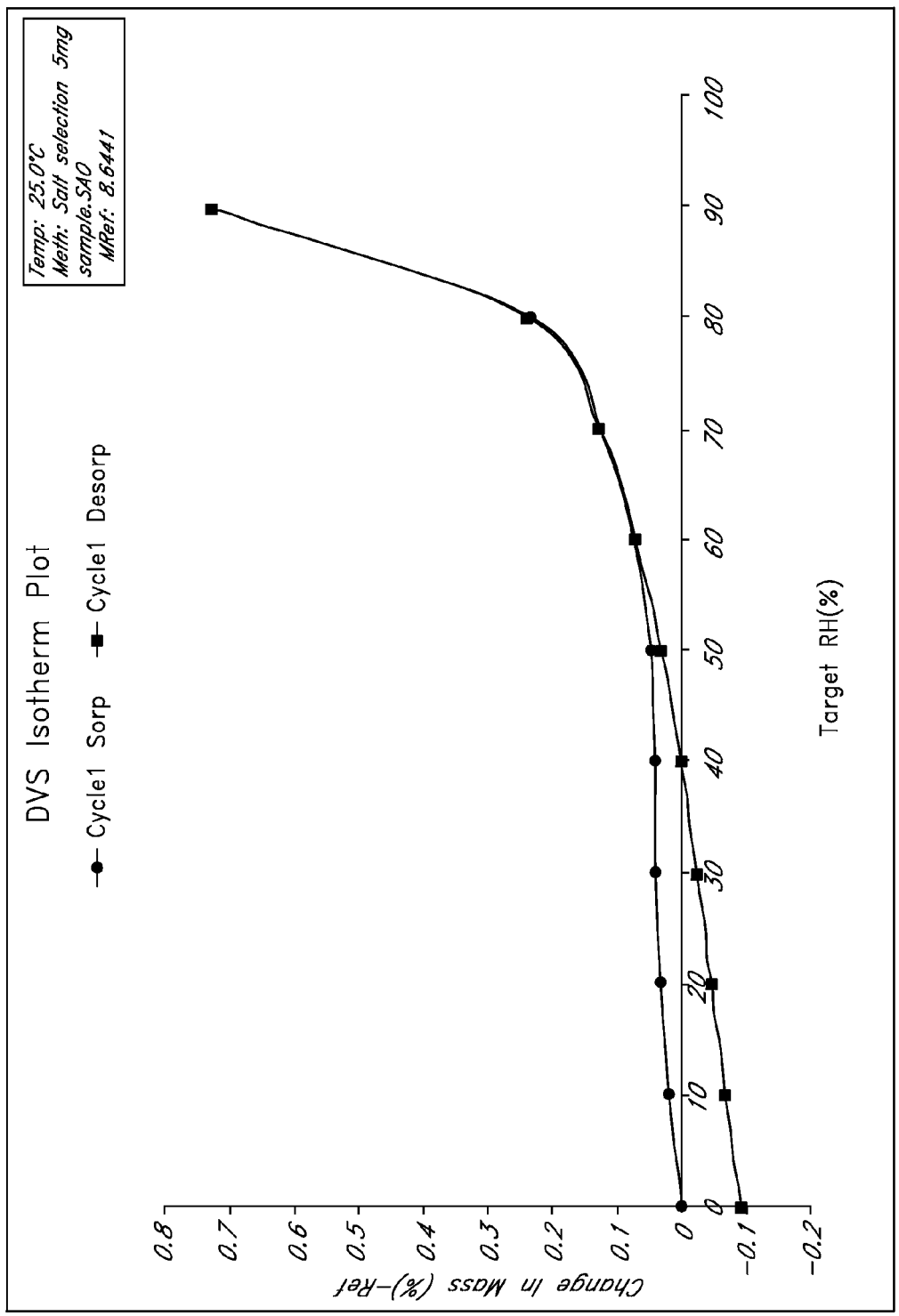
FIG. 20 shows dynamic vapor sorption results for Form V.

FIG. 19 shows nuclear magnetic resonance (NMR) integrals and chemical shifts for Form V. The integrals confirm the presence of L-ornithine phenyl acetate: 7.5 (aromatic CH), 3.8 (CH adjacent to NH2), 3.6 (CH2 unit of phenyl acetate), 3.15 (CH2 adjacent to NH2) and 1.9 (aliphatic CH2 units) ppm (integrals: 5:1:2:2:4 protons; 4.2, 0.8, 1.7, 1.7, 3.0). Amine protons and hydroxylprotons were not observed due to proton exchange at both the zwitterion and site of salt formation. Meanwhile, FIG. 19 shows dynamic vapor sorption (DVS) results for Form V, and show a water uptake of about 0.75% by weight. XRPD results following DVS analysis (not shown) suggest that Form V transitioned to Form II, but the chemical composition was unchanged. Form V is therefore characterized as non-hygroscopic, but not stable over a wide range of humidity.

A 7-day stability study of Form V at 40° C./75% RH indicated that a transformation to Form II occurred under these conditions; however the chemical composition was unchanged. Accordingly, Form V is most likely metastable.

EXAMPLES AND EXPERIMENTAL METHODS

Additional embodiments are disclosed in further detail in the following examples, which are not in any way intended to limit the scope of the claims.

Example 1

Small-scale Batch Process to Produce L-Ornithine Phenyl Acetate

About 8.4 g (0.049 moles) of L-ornithine hydrochloride was dissolved in 42 mL $H_2O$ and, separately, about 11.4 g of silver benzoate was dissolved in 57 mL DMSO. Subsequently, the silver benzoate solution was added to the L-ornithine hydrochloride solution. Combining the two mixtures resulted in an immediate, exothermic precipitation of a creamy white solid (AgCl). The solid was removed by vacuum filtration and retaining the filtrate (L-ornithine benzoate in solution). 200 mL of IPA was added to the filtrate and the mixture was cooled to 4° C. A crystalline solid precipitated after about 3 hours (L-ornithine benzoate) which was isolated by vacuum filtration. Yield: 60%.

7.6 g (0.03 moles) of the L-ornithine benzoate was dissolved in 38 mL $H_2O$ and about 4.4 g of sodium phenyl acetate was dissolved 22 mL $H_2O$, Subsequently, the sodium phenyl acetate solution was added to the L-ornithine benzoate solution and left to stir for about 10 minutes. About 240 mL of IPA (8:2 IPA:$H_2O$) was added and the solution stirred for 30 minutes before cooling to 4° C. A crystalline solid precipitated after about 3 hours at 4° C. (L-ornithine phenyl acetate). The precipitate was isolated by vacuum filtration and washed with 48-144 mL of IPA. Yield: 57%.

Example 2

Large-scale Batch Process to Produce L-Ornithine Phenyl Acetate

Two separate batches of L-ornithine phenyl acetate were prepared as follows:

About 75 kg of L-Ornithine monohydrochloride was dissolved in 227 kg of water. To the resulting solution was added 102 kg of silver benzoate dissolved in 266 kg of DMSO at room temperature within 2 hours. Initially, a strong exothermy was observed and the silver chloride precipitated. The receiver containing the solution was then washed with 14 kg of DMSO that was added to the reaction mass. In order to remove the silver chloride formed, the reaction mass was filtered over a lens filter prepared with 10 kg of Celite and a GAF filter of 1 mm. After filtration, the filter was washed with an additional 75 kg of water. The reaction mass was placed in a different tank after filtration to prevent contamination with residual silver chloride. The reaction mass was then heated at 35±2° C. and 80 kg of sodium phenyl acetate was added. At this point the reaction mass was stirred at 35±2° C. for at least 30 minutes.

In order to precipitate the final product, 353 kg of IPA was added to the reaction mass. The reaction mass was then cooled to 0±3° C. within 6 hours, stirred for 1 hour and then the product isolated in a centrifuge.

About 86 kg of final wet product was obtained. The product was then dried at 40±5° C. for about 6.5 to 8 hours to provide about 75 kg of L-ornithine phenyl acetate. Yield: 63.25%. TABLE 5 summarizes measurements relating to the final product.

TABLE 5

Analytical Results for Large-scale Batch Process

| Test | Batch 1 | Batch 2 |
| --- | --- | --- |
| Purity | 98.80% | 98.74% |
| Benzoate | 0.17% | 0.14% |
| Silver | 28 ppm | 157 ppm |
| Chloride | 0.006% | 0.005% |
| Sodium | 7 ppm | 26 ppm |
| Total Impurities | 0.17% | 0.14% |
| Physical Form | Form II | Form II |

Example 3

Preparing Sodium Phenyl Acetate Solution In Situ

Phenyl acetic acid (PAA) was dissolved in a solution of isopropanol. About 1 molar equivalent of sodium hydroxide was added to the solution and stirred. The obtained solution was added dropwise to a solution having about 1 molar equivalent of L-ornithine benzoate. L-ornithine phenyl acetate was precipitated from this solution using generally the same procedures described in Example 2. Yield: 53.5%. The white powder was further characterized and is summarized in TABLE 6 under the heading "Trial A."

Example 4

Water/IPA Solvent Ratios for Isolating L-Ornithine Phenyl Acetate

Several studies were completed to consider the effect of the solvent composition on the yield and product purity. The trials were completed using a similar protocol to Examples 2 and 3 and detailed in TABLE 6.

Trials A, B, and D include various ratios of water/IPA and demonstrate that yield can be improved by increasing the relative amount of IPA. Trial D crystallized the product upon intermixing the IPA, while Trials A and B include cooling the solution to obtain the product. In addition, Trial F demonstrates that reducing the volume of reaction mass may also facilitate precipitation of the final product.

Trials C, E, and G include a distillation step to remove water from the reaction mass prior to adding IPA. The yield for Trials C, E, and G was 70.0%, 51.2%, and 68.0%, respectively.

TABLE 6

Experimental Results for Water/IPA ratio

| Trial | Description | Water/IPA ratio | Precipitation Conditions | Yield (%) | Product Description |
|---|---|---|---|---|---|
| TRIAL A | solvent ratio for final product | 41:59 | during cooling to 0° C. | 53.5% | white powder |
| TRIAL B | precipitation similar to Examples 2, 3 | 46:54 | | 50.5% | white powder |
| TRIAL C | distillation introduced prior to IPA dosage | Unknown | during distillation | 70.0% | off-white powder |
| TRIAL D | increased IPA ratio to improve yield | 30:70 | during IPA dosage | 61.2% | white powder |
| TRIAL E | distillation introduced prior to IPA addition to concentrate mass | Unknown | during IPA dosage | 51.2% | white powder |
| TRIAL F | decreased water/IPA volume to facilitate product precipitation | 46:54 | during IPA dosage | 51.5% | white powder |
| TRIAL G | decreased water ratio and introduced distillation after filtering | 35:65 | during PAA dosage | 68.0% | white powder |

Example 5

Reducing Silver Content in L-Ornithine Phenyl Acetate

Batch 2 from Example 2 exhibited higher amounts of silver (157 ppm), and therefore procedures were tested for reducing the silver content. Nine trials were completed; each generally including dissolving about 20 g of L-ornithine phenyl acetate from Batch 2 into 1.9 parts water, and then subsequently adding 10.8 parts IPA. A crystalline form was isolated at 0° C. by filtration.

For four trials, 8.0 mg or 80 mg of heavy metal scavengers SMOPEX 102 or SMOPEX 112 were added to the aqueous solution and stirred for 2 hours. The scavengers failed to reduce the silver content below 126 ppm. In still another trial, the L-ornithine phenyl acetate was crashed out in a solution of IPA, rather than crystallized; however this trial also failed to reduce the silver content below 144 ppm.

The last three trials included adding diluted HCl to the solution to precipitate remaining amount of silver as AgCl. The precipitate was then removed by filtration. The three trials included adding: (1) 1.0 g of 0.33% HCl at 20° C.; (2) 1.0 g of 0.33% HCl at 30° C.; and (3) 0.1 g of 3.3% HCl at 20° C. The three trials reduced the silver content to 30 ppm, 42 ppm, and 33 ppm, respectively, and each trial yielding greater than 90% L-ornithine phenyl acetate. Accordingly, the addition of HCl was effective in reducing the amount of residual silver.

Example 6

Process for Preparing L-Ornithine Phenyl Acetate from L-Ornithine Free Base by Using an Alkali Metal Alkoxide Base As a general procedure, L-ornithine hydrochloride was suspended in a solvent. Subsequently, the reaction mass was heated and a base, sodium methoxide, was added. NaCl formed and was removed from the system by filtration. The reaction mass was cooled and a molar equivalent of phenyl acetic acid was added to the reaction mass to form L-ornithine phenyl acetate. The final product was isolated, washed and dried. A summary of the trials for this process is provided in TABLE 7.

TABLE 7

Process Trials

| Trial | Base | Eq. of Base | Solvent |
|---|---|---|---|
| 1 | NaOMe 21% in MeOH | 1.0 eq. | MeOH |
| 2 | NaOMe 21% in MeOH | 0.95 eq. | IPA |
| 3 | NaOMe 21% in EtOH | 1.0 eq. | EtOH |
| 4 | NaOMe 21% in MeOH | 1.0 eq. | MeOH |
| 5 | NaOMe 21% in MeOH | 1.0 eq. | MeOH w/IPA for precipitation |
| 6 | NaOMe 21% in MeOH | 1.0 eq. | Acetonitrile |
| 7 | NaOMe 21% in MeOH | 1.0 eq. | Water/IPA |
| 8 | NaOMe 21% in MeOH | 1.0 eq. | Water/IPA |
| 9 | NaOMe 21% in MeOH | 1.0 eq. | n-butanol |

The resulting L-ornithine phenyl acetate was found to exhibit high amounts of chloride (at least about 1% by weight), and presumably include similar amounts of sodium. The yields were about 50% for Trials 2, 4, and 5.

Example 7

Process for Preparing L-Ornithine Phenyl Acetate without an Intermediate Salt

Further studies were completed using generally the same procedure as Example 6. The results are shown in TABLE 8:

TABLE 8

Additional Process Trials

| | Trial I | Trial II | Trial III | Trial IV |
|---|---|---|---|---|
| Trial description | 1 eq of MeONa in 10.6 p of MeOH | 1 eq of MeONa in 10.6 p of i-PrOH | 1 eq of MeONa in 15 p of i-PrOH | 0.5 eq of Ca(OH)$_2$ in 10.6 p of EtOH |

TABLE 8-continued

Additional Process Trials

| | Trial I | Trial II | Trial III | Trial IV |
|---|---|---|---|---|
| Yield | 47.2% | 41.9% | 57.6% | 40.2% |
| Description | white powder | white powder | off-white powder | white powder |

Example 8

Process for Preparing L-Ornithine Phenyl Acetate from L-Ornithine Free Base by Using a Carbonate Base 1 part L-ornithine hydrochloride by mole was suspended in about 10.6 parts ethanol. Subsequently, the reaction mass (suspension) was heated to about 50° C. and about 1 part calcium carbonate was added. The reaction mass was stirred for about 2 hours. The free L-ornithine base was isolated by filtration to obtain a powder, while the $CaCl_2$ remained in solution. The filtered powder was dissolved in water and filtered to remove unreacted calcium carbonate. About 1 part phenyl acetic acid by mole in isopropanol was intermixed with the aqueous L-ornithine solution. The final product precipitated from solution and was isolated, washed, and dried. Yield: 44.5%.

Example 9

Process for Preparing L-Ornithine Phenyl Acetate from L-Ornithine Free Base by Using an Inorganic Base 1 part L-ornithine hydrochloride by mole was suspended in about 10.6 parts ethanol. Subsequently, the reaction mass (suspension) was heated to about 50° C. and about 0.5 part calcium hydroxide by mole was added. The reaction mass was stirred for about 1.5 hours. The free L-ornithine base was isolated by filtration and washed with ethanol. The filtered solid was dissolved in water and phenyl acetic acid (1.0 equivalent) in isopropanol was added dropwise to the aqueous L-ornithine solution at room temperature. After at least 30 minutes stiffing at room temperature, IPA was added to precipitate the final product. The final product was isolated, washed, and dried. Yield: 43.95%.

Alternatively, L-ornithine free base was also prepared in an aqueous solution. 1 part L-ornithine hydrochloride by mole was dissolved in about 4.1 parts water. Subsequently, about 0.5 part calcium hydroxide by mole was added to the solution and stirred for about 30 minutes. The free L-ornithine base was then not isolated by filtration. Next, about 1 part phenyl acetic acid in isopropanol was intermixed with the aqueous L-ornithine solution. The final product precipitated from solution was isolated, washed, and dried. Yield: >100%.

Example 10

Process for Preparing L-Ornithine Phenyl Acetate from L-Ornithine Free Base by Using Barium Hydroxide To 1.0 equivalent of L-ornithine hydrochloride in an aqueous solution was added 2.7 molar equivalent of barium hydroxide. Subsequently, the reaction mass was refluxed for 2 hours and then cooled to room temperature. Sulfuric acid (6N) was added slowly to acidify the resulting reaction mass until pH was about 1.5. The insoluble barium sulfate formed was filtered through by using a 0.2 µm filter. The filtrate was then concentrated by distillation and neutralized to pH 7-7.5 by adding a barium hydroxide solution. The barium sulfate salt formed was removed again. Finally, a solution of phenyl acetic acid (1.13 equivalents) with sodium hydroxide in IPA was added at 35° C. to the resulting solution at 35° C. IPA was added and the reaction mixture was cooled to 0° C. to in order to precipitate the final product. The final product was isolated by filtration, washed with a mixture of water and IPA, and dried. Yield: 37.2%.

Example 11

Process for Preparing L-Ornithine Phenyl Acetate via an Acetate Intermediate

Dissolve 25 mg of L-ornithine hydrochloride in 5 vols of $H_2O$, and then add excess acetic acid (about 5 vols) to form a slurry. Subject the slurry to temperature cycling between 25° C. and 40° C. every 4 hours for about 3 days. Add 1 equivalent of phenyl acetic acid (with respect to L-ornithine) and stir for about 4-6 hours (possibly heat). Use IPA as an anti-solvent, add enough to obtain a ratio of 70:30 (IPA:$H_2O$). Isolate by vacuum filtration and dry for about 4-8 hours at 80° C. to remove any residual acetic acid.

Example 12

Process for Preparing L-Ornithine Phenyl Acetate from Halide L-Ornithine Salt and Phenyl Acetate Salt L-ornithine monohydrochloride is dissolved in water at a concentration of 300-350 g/Kg (~3 volumes water). To the resulting solution is added 1 molar equivalent of silver phenyl acetate in 2.5 volumes DMSO (0.4 g/g) at room temperature within 2 hours. The receiver containing the solution is then washed with DMSO and added to the reaction mass. The silver chloride formed can be filtered through the reaction mass over a lens filter prepared with Celite and a GAF filter. After filtration, the filter is washed with an additional volume of water.

In order to precipitate the final product, IPA is added to the reaction mass to a final concentration range of 65-95% IPA. The reaction mass is then cooled to 0 ±3° C. within 6 hours, stirred for 1 hour and then the product isolated in a centrifuge.

The isolated wet product is redissolved in an aqueous dilute HCl solution (0.33%) representing between 1-3.5 molar equivalents of HCl. The reaction mass is filtered over a lens filter prepared with Celite and a GAF filter to remove the silver chloride formed. After filtration, the filter is washed with an additional volume of water.

To precipitate the final product, IPA is added again to the reaction mass to a final concentration range of 60-80% IPA. The reaction mass is then cooled to 0±3° C. within 6 hours, stirred for 1 hour and then the product is isolated in a centrifuge. The final product is then dried at 40±5° C. for about 6.5 to 8 hours to provide crystalline L-ornithine phenyl acetate.

What is claimed is:

1. A process for making L-ornithine phenyl acetate salt comprising:
    preparing a solution of phenyl acetate salt by mixing a phenyl acetic acid and a base in a solvent;
    intermixing L-ornithine benzoate with the solution of phenyl acetate salt; and isolating a composition comprising L-ornithine phenyl acetate.

2. The process of claim 1, further comprising forming L-ornithine benzoate, wherein forming L-ornithine benzoate comprises intermixing an L-ornithine salt, a benzoate salt and a first solvent to form an intermediate solution.

3. The process of claim 2, further comprising removing at least a portion of a salt from said intermediate solution before intermixing with the phenyl acetate salt, wherein said removed salt is not an L-ornithine salt.

4. The process of claim 3, wherein said removed salt comprises an anion derived at least in part from the L-ornithine salt and a cation derived at least in part from the benzoate salt.

5. The process of claim 4, wherein the L-ornithine salt is L-ornithine hydrochloride and said anion is chloride.

6. The process of claim 4, wherein the benzoate salt is silver benzoate and the cation is a silver ion.

7. The process of claim 3, wherein the process further comprises adding hydrochloric acid before said removing at least a portion of the salt.

8. The process claim 3, wherein at least about 90% by weight of said removed salt is removed.

9. The process of claim 1, further comprising forming L-ornithine benzoate, wherein forming L-ornithine benzoate comprises:
intermixing an L-ornithine salt, a benzoate salt and a first solvent to form an intermediate solution; and
isolating L-ornithine benzoate from said intermediate solution.

10. The process of claim 9, further comprising removing at least a portion of a salt from said intermediate solution before isolating the L-ornithine benzoate, wherein said removed salt is not an L-ornithine salt.

11. The process of claim 10, wherein the process further comprises adding hydrochloric acid before said removing at least a portion of the salt.

12. The process of claim 9, wherein isolating L-ornithine benzoate comprises crystallizing L-ornithine benzoate from said intermediate solution.

13. The process of claim 1, wherein the base is selected from the group consisting of an alkali metal hydroxide and an alkali metal alkoxide.

14. The process of claim 1, further comprising forming L-ornithine benzoate, wherein forming L-ornithine benzoate comprises intermixing an L-ornithine salt, a benzoate salt and a second solvent to form an intermediate solution.

15. The process of claim 1, wherein said composition comprises at least about 0.10% by weight benzoate salt and no more than 5% by weight benzoate salt.

16. The process of claim 14, wherein the L-ornithine salt is L-ornithine hydrochloride.

17. The process of claim 14, wherein the benzoate salt is silver benzoate.

18. The process of claim 17, wherein said composition further comprises at least 10 ppm silver and no more than 600 ppm silver.

19. The process of claim 1, wherein the phenyl acetate salt is an alkali metal salt.

20. The process of claim 19, wherein the alkali metal salt is sodium phenyl acetate.

21. The process of claim 20, wherein said composition comprises no more than 100 ppm sodium.

22. The process of claim 21, wherein said composition comprises no more than 20 ppm sodium.

23. The process of claim 1, wherein the composition comprises no more than 0.1% by weight chloride.

24. The process of claim 1, wherein the composition comprises a crystalline form exhibiting an X-ray powder diffraction pattern comprising at least one characteristic peak, wherein said characteristic peak is selected from the group consisting of approximately 6.0°, 13.9°, 14.8°, 17.1°, 17.8° and 24.1° 2θ.

25. A process for making L-ornithine phenyl acetate salt comprising:
intermixing an L-ornithine salt, silver phenyl acetate and a solvent to form a solution; and
isolating a composition comprising L-ornithine phenyl acetate from said solution.

26. The process of claim 25, wherein the L-ornithine salt is a halide salt.

27. The process of claim 26, wherein the L-ornithine salt is L-ornithine hydrochloride.

28. The process of claim 25, further comprising preparing the silver phenyl acetate by mixing a phenyl acetic acid and a base in a solvent.

29. The process of claim 25, wherein the process further comprises adding hydrochloric acid to the solution before isolating L-ornithine phenyl acetate from the solution.

30. The process of claim 25, wherein said composition further comprises at least 10 ppm silver and no more than 600 ppm silver.

31. The process of claim 25, wherein said composition comprises no more than 100 ppm sodium.

32. The process of claim 31, wherein said composition comprises no more than 20 ppm sodium.

33. The process of claim 25, wherein the composition comprises no more than 0.1% by weight chloride.

34. The process of claim 25, wherein the composition comprises a crystalline form exhibiting an X-ray powder diffraction pattern comprising at least one characteristic peak, wherein said characteristic peak is selected from the group consisting of approximately 6.0°, 13.9°, 14.8°, 17.1°, 17.8° and 24.1°2θ.

\* \* \* \* \*